(12) United States Patent
Doidge et al.

(10) Patent No.: US 9,179,854 B2
(45) Date of Patent: Nov. 10, 2015

(54) THREE-DIMENSIONAL LOCALIZATION, DISPLAY, RECORDING, AND ANALYSIS OF ELECTRICAL ACTIVITY IN THE CEREBRAL CORTEX

(76) Inventors: Mark S. Doidge, Toronto (CA); Joseph D. Mocanu, Toronto (CA)

( * ) Notice: Subject to any disclaimer, the term of this patent is extended or adjusted under 35 U.S.C. 154(b) by 934 days.

(21) Appl. No.: 11/981,114

(22) Filed: Oct. 31, 2007

(65) Prior Publication Data
US 2010/0042011 A1 Feb. 18, 2010

Related U.S. Application Data

(63) Continuation of application No. PCT/CA2006/000776, filed on May 16, 2006.

(60) Provisional application No. 60/681,140, filed on May 16, 2005.

(51) Int. Cl.
A61B 5/04 (2006.01)
A61B 5/0476 (2006.01)
A61B 5/16 (2006.01)

(52) U.S. Cl.
CPC ............... *A61B 5/0476* (2013.01); *A61B 5/164* (2013.01)

(58) Field of Classification Search
CPC .................................................... A61B 5/0476
USPC ................................................. 600/544–545
See application file for complete search history.

(56) References Cited

U.S. PATENT DOCUMENTS 3,855,998 A 12/1974 Hidalgo-Briceno
4,608,635 A 8/1986 Osterholm
(Continued)

FOREIGN PATENT DOCUMENTS

EP 0 598 478 5/1994
EP 2685443 A1 1/2014
(Continued)

*Primary Examiner* — Michael D'Angelo
*Assistant Examiner* — Christian Jang
(74) *Attorney, Agent, or Firm* — Tarolli, Sundheim, Covell & Tummino LLP

(57) ABSTRACT

The present invention describes a method and apparatus to localize the electrical signals measured from a subject's scalp surface, preferably in near-real time, and to generate dynamic three-dimensional information of the electrical activity occurring within the cerebral cortex of the brain. In the preferred embodiment, it can produce images that can be immediately inspected and analyzed by an operator in near-real time, resulting in a powerful new cortical imaging modality, which we denote as Dynamic Electrocortical Imaging (DECI). The present invention involves the use of a computer, an electroencephalographic (EEG) amplifier, EEG electrodes, and custom software. It can measure healthy and diseased cortical events and states in both conscious and unconscious subjects. This is useful, as it allows for the diagnosis, monitoring and treatment of cortical disorders, while also furthering the understanding of the human brain and lending use to additional non-medical applications such as in entertainment, education, lie-detection and industry. The invention in one embodiment is implemented using software in conjunction with readily available EEG hardware. Furthermore, this same method can be applied to pre-existing data and when doing so, EEG hardware is not required. Having a practical near-real time 3D imaging system brings a far more accessible technology to doctors, researchers, individuals, and private clinics to better diagnose, monitor, treat and understand many of the conditions and abnormalities of the brain.

24 Claims, 20 Drawing Sheets

(56) References Cited

U.S. PATENT DOCUMENTS

| | | |
|---|---|---|
| 4,949,725 A | 8/1990 | Raviv et al. |
| 5,309,923 A | 5/1994 | Leuchter et al. |
| 5,564,433 A | 10/1996 | Thornton |
| 6,097,980 A | 8/2000 | Monastra et al. |
| 6,240,308 B1 | 5/2001 | Hardy et al. |
| 6,370,414 B1 | 4/2002 | Robinson |
| 6,574,513 B1 | 6/2003 | Collura et al. |
| 7,756,938 B2 | 7/2010 | Edmonds et al. |
| 7,840,248 B2 | 11/2010 | Fuchs et al. |
| 7,999,684 B2 | 8/2011 | Fenkanyn et al. |
| 8,561,163 B2 | 10/2013 | Jain et al. |
| 2002/0091335 A1* | 7/2002 | John et al. .................... 600/544 |
| 2003/0093004 A1* | 5/2003 | Sosa et al. .................... 600/544 |
| 2007/0066914 A1 | 3/2007 | Le et al. |
| 2007/0173733 A1 | 7/2007 | Le et al. |
| 2007/0179396 A1 | 8/2007 | Le et al. |
| 2007/0225585 A1 | 9/2007 | Washbon et al. |
| 2008/0159365 A1 | 7/2008 | Dubocanin et al. |
| 2008/0218472 A1 | 9/2008 | Breen et al. |
| 2008/0270364 A1 | 10/2008 | Bayardo et al. |
| 2009/0105576 A1 | 4/2009 | Do et al. |
| 2009/0259137 A1 | 10/2009 | Delic et al. |
| 2010/0201870 A1 | 8/2010 | Luessi et al. |
| 2012/0259604 A1 | 10/2012 | Ouarti et al. |
| 2013/0216985 A1 | 8/2013 | de Villers-Sidani et al. |

FOREIGN PATENT DOCUMENTS

| | | |
|---|---|---|
| JP | 07059742 | 7/1995 |
| WO | 2005031556 A1 | 4/2005 |
| WO | 2008109699 A2 | 9/2008 |
| WO | 2009087486 A2 | 7/2009 |
| WO | 2012064999 A1 | 5/2012 |
| WO | 2013041152 A1 | 3/2013 |
| WO | 2013153137 A1 | 10/2013 |
| WO | 2013160255 A1 | 10/2013 |

* cited by examiner $$\begin{pmatrix} v_1e_1x & v_1e_2x & \dots & v_1e_{32}x & v_1e_1y & v_1e_2y & \dots & v_1e_{32}y & v_1e_1z & v_1e_2z & \dots & v_1e_{32}z \\ v_2e_1x & v_2e_2x & \dots & v_2e_{32}x & v_2e_1y & v_2e_2y & \dots & v_2e_{32}y & v_2e_1z & v_2e_2z & \dots & v_2e_{32}z \\ & & & & \dots\dots\dots \\ & & & & \dots\dots\dots \\ & & & & \dots\dots\dots \\ v_{2393}e_1x & v_{2393}e_2x & \dots & v_{2393}e_{32}x & v_{2393}e_1y & v_{2393}e_2y & \dots & v_{2393}e_{32}y & v_{2393}e_1z & v_{2393}e_2z & \dots & v_{2393}e_{32}z \\ v_{2394}e_1x & v_{2394}e_2x & \dots & v_{2394}e_{32}x & v_{2394}e_1y & v_{2394}e_2y & \dots & v_{2394}e_{32}y & v_{2394}e_1z & v_{2394}e_2z & \dots & v_{2394}e_{32}z \end{pmatrix}$$

T $$X \begin{pmatrix} e_1 \\ e_2 \\ \dots \\ \dots \\ e_{31} \\ e_{32} \\ e_1 \\ e_2 \\ \dots \\ \dots \\ e_{31} \\ e_{32} \\ e_1 \\ e_2 \\ \dots \\ \dots \\ e_{31} \\ e_{32} \end{pmatrix} = \begin{pmatrix} v_1x \\ v_2x \\ \dots \\ \dots \\ v_{2393}x \\ v_{2394}x \\ v_1y \\ v_2y \\ \dots \\ \dots \\ v_{2393}y \\ v_{2394}y \\ v_1z \\ v_2z \\ \dots \\ \dots \\ v_{2393}z \\ v_{2394}z \end{pmatrix}$$

E     V

Where:

$v_n$ = for voxel $n$
$e_n$ = for EEG electrode $n$
x/y/z = x/y/z component

*For each frame of EEG:*

Transformation Matrix (T) x EEG (E) = X,Y, Z Vector Components for Each Voxel (V)

T x E = V

Example depicted here utilizes 32 electrodes for the EEG input, and 2394 voxels for the solution space

Figure 2

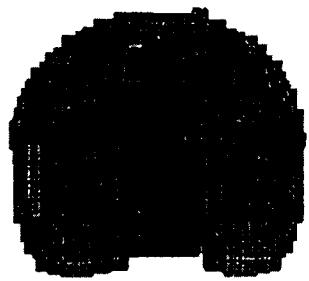
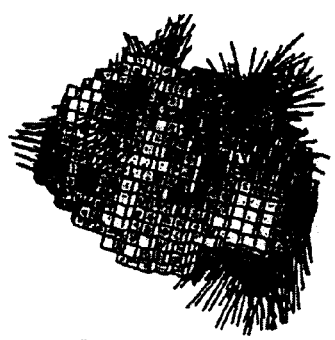
Figure 5A | Figure 5B
 
Figure 5C
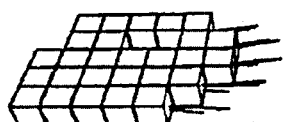 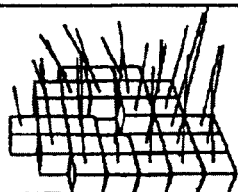
Figure 5D
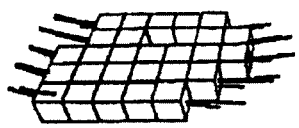 
Figure 5E
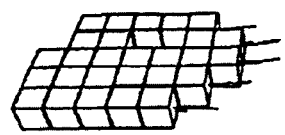 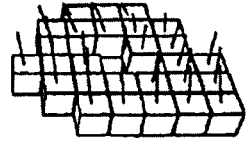
Figure 5F

Voxel Table: 1
Current Voxel 2328
Density = 0.7760 mA/m^2
X: -3   Y: -11,   Z: 64
Left Brodmann area 6
Medial Frontal Gyrus
Frontal Lobe
☐ Live          ☐ Track Max
| Select Max | Refresh |
| ROI Dialog | Select Voxels |

FIG. 6G

| Voxel | Side | Brodmann Area | Major Anatomy | Minor Anatomy | Magnitude | X | Y | Z |
|---|---|---|---|---|---|---|---|---|
| 1 | Left | Brodmann area 20 | Temporal Lobe | Inferior Temporal Gyrus | 0.155656 | -0.0006 | -6.47E-05 | -0.00016 |
| 2 | Left | Brodmann area 20 | Temporal Lobe | Inferior Temporal Gyrus | 0.160606 | -0.00061 | -5.54E-05 | -0.00013 |
| 3 | Left | Brodmann area 20 | Limbic Lobe | Uncus | 0.15346 | -0.00057 | -4.97E-05 | -6.33E-05 |
| 4 | Left | Brodmann area 20 | Limbic Lobe | Uncus | 0.139398 | -0.00051 | -5.00E-05 | -1.53E-05 |
| 5 | Right | Brodmann area 20 | Limbic Lobe | Uncus | 0.13315 | -0.00026 | -1.73E-05 | 0.000643 |
| 6 | Right | Brodmann area 20 | Temporal Lobe | Inferior Temporal Gyrus | 0.146844 | -0.00033 | -6.72E-06 | 0.000734 |
| 7 | Right | Brodmann area 20 | Temporal Lobe | Inferior Temporal Gyrus | 0.143223 | -0.00036 | -0.00012 | 0.000744 |
| 8 | Right | Brodmann area 20 | Temporal Lobe | Inferior Temporal Gyrus | 0.119993 | -0.00031 | -0.00014 | 0.000636 |
| 9 | Left | Brodmann area 20 | Temporal Lobe | Inferior Temporal Gyrus | 0.15607 | -0.00061 | -0.00014 | -0.00021 |
| 10 | Left | Brodmann area 20 | Temporal Lobe | Inferior Temporal Gyrus | 0.162513 | -0.00058 | -0.00014 | -0.00016 |
| 11 | Left | Brodmann area 20 | Temporal Lobe | Inferior Temporal Gyrus | 0.152428 | -0.00053 | -0.00012 | -9.81E-05 |
| 12 | Left | Brodmann area 20 | Limbic Lobe | Uncus | 0.150762 | -0.00051 | -0.0001 | -3.11E-05 |
| 13 | Left | Brodmann area 36 | Limbic Lobe | Uncus | 0.11754 | -0.00039 | -6.41E-05 | 6.52E-06 |
| 14 | Right | Brodmann area 36 | Limbic Lobe | Uncus | 0.1199 | -0.00022 | 6.38E-05 | 0.000671 |
| 15 | Right | Brodmann area 20 | Limbic Lobe | Uncus | 0.14977 | -0.00031 | 3.81E-05 | 0.000738 |
| 16 | Right | Brodmann area 20 | Temporal Lobe | Inferior Temporal Gyrus | 0.160173 | -0.00039 | -6.82E-06 | 0.000822 |
| 17 | Right | Brodmann area 20 | Temporal Lobe | Inferior Temporal Gyrus | 0.15987 | -0.00044 | -4.56E-05 | 0.000695 |
| 18 | Right | Brodmann area 20 | Temporal Lobe | Inferior Temporal Gyrus | 0.137745 | -0.00038 | -7.14E-06 | 0.000699 |
| 19 | Left | Brodmann area 21 | Temporal Lobe | Middle Temporal Gyrus | 0.151142 | -0.00051 | -0.00021 | -0.00021 |
| 20 | Left | Brodmann area 38 | Temporal Lobe | Middle Temporal Gyrus | 0.178599 | -0.00055 | -0.00026 | -0.00021 |
| 21 | Left | Brodmann area 20 | Temporal Lobe | Inferior Temporal Gyrus | 0.157821 | -0.00047 | -0.00021 | -0.00014 |
| 22 | Left | Brodmann area 20 | Limbic Lobe | Inferior Temporal Gyrus | 0.137127 | -0.0004 | -0.00016 | -6.99E-05 |
| 23 | Left | Brodmann area 36 | Limbic Lobe | Uncus | 0.106267 | -0.00033 | -0.0001 | -1.08E-05 |
| 24 | Right | Brodmann area 36 | Limbic Lobe | Uncus | 0.080639 | -0.00014 | 7.62E-05 | 0.000376 |
| 25 | Right | Brodmann area 38 | Limbic Lobe | Uncus | 0.119236 | -0.00022 | 0.00011 | 0.000575 |
| 26 | Right | Brodmann area 20 | Temporal Lobe | Middle Temporal Gyrus | 0.125209 | -0.00027 | 0.000107 | 0.000647 |
| 27 | Right | Brodmann area 38 | Temporal Lobe | Middle Temporal Gyrus | 0.197946 | -0.00033 | 9.82E-05 | 0.000726 |
| 28 | Right | Brodmann area 21 | Temporal Lobe | Middle Temporal Gyrus | 0.147067 | -0.00041 | 6.22E-05 | 0.000806 |
| 29 | Right | Brodmann area 21 | Temporal Lobe | Middle Temporal Gyrus | 0.112265 | -0.00033 | 3.06E-05 | 0.000629 |
| 30 | Left | Brodmann area 21 | Temporal Lobe | Middle Temporal Gyrus | 0.153941 | -0.00039 | -0.0003 | -0.00019 |
| 31 | Left | Brodmann area 38 | Temporal Lobe | Middle Temporal Gyrus | 0.176319 | -0.0004 | -0.00032 | -0.00017 |
| 32 | Left | Brodmann area 38 | Temporal Lobe | Superior Temporal Gyrus | 0.146467 | -0.00033 | -0.00026 | -0.00011 |
| 33 | Right | Brodmann area 38 | Temporal Lobe | Superior Temporal Gyrus | 0.099438 | -0.00017 | 0.000131 | 0.000492 |
| 34 | Right | Brodmann area 38 | Temporal Lobe | Superior Temporal Gyrus | 0.12686 | -0.00023 | 0.000201 | 0.000659 |
| 35 | Right | Brodmann area 38 | Temporal Lobe | Middle Temporal Gyrus | 0.136369 | -0.00027 | 0.000223 | 0.000732 |
| 36 | Right | Brodmann area 21 | Temporal Lobe | Middle Temporal Gyrus | 0.121976 | -0.00028 | 0.000179 | 0.000665 |
| 37 | Left | Brodmann area 38 | Temporal Lobe | Superior Temporal Gyrus | 0.136724 | -0.00025 | -0.00028 | -0.00012 |
| 38 | Left | Brodmann area 38 | Temporal Lobe | Superior Temporal Gyrus | 0.127924 | -0.00023 | -0.00025 | -9.59E-05 |
| 39 | Right | Brodmann area 38 | Temporal Lobe | Superior Temporal Gyrus | 0.099676 | -0.00015 | 0.000197 | 0.000511 |
| 40 | Right | Brodmann area 38 | Temporal Lobe | Superior Temporal Gyrus | 0.103814 | -0.00016 | 0.000212 | 0.00054 |
| 41 | Left | Brodmann area 20 | Temporal Lobe | Fusiform Gyrus | 0.157051 | -0.00062 | 2.03E-05 | -0.00014 |
| 42 | Left | Brodmann area 20 | Temporal Lobe | Inferior Temporal Gyrus | 0.163677 | -0.00072 | 2.28E-05 | -0.00013 |
| 43 | Left | Brodmann area 20 | Temporal Lobe | Inferior Temporal Gyrus | 0.163829 | -0.00066 | 3.43E-05 | -5.95E-05 |
| 44 | Left | Brodmann area 20 | Temporal Lobe | Inferior Temporal Gyrus | 0.162078 | -0.00063 | 3.07E-05 | 9.41E-06 |
| 45 | Left | Brodmann area 20 | Limbic Lobe | Uncus | 0.146614 | -0.00056 | 1.33E-05 | 4.50E-05 |
| 46 | Right | Brodmann area 20 | Limbic Lobe | Uncus | 0.126674 | -0.00013 | -6.76E-05 | 0.000657 |
| 47 | Right | Brodmann area 20 | Temporal Lobe | Inferior Temporal Gyrus | 0.137246 | -0.00015 | -0.00013 | 0.000621 |
| 48 | Right | Brodmann area 20 | Temporal Lobe | Inferior Temporal Gyrus | 0.134716 | -0.00015 | -0.00021 | 0.00063 |
| 49 | Right | Brodmann area 20 | Temporal Lobe | Inferior Temporal Gyrus | 0.130502 | -0.00013 | -0.00027 | 0.000623 |
| 50 | Right | Brodmann area 20 | Temporal Lobe | Fusiform Gyrus | 0.104212 | -6.59E-05 | -0.00026 | 0.000492 |

FIG. 6H

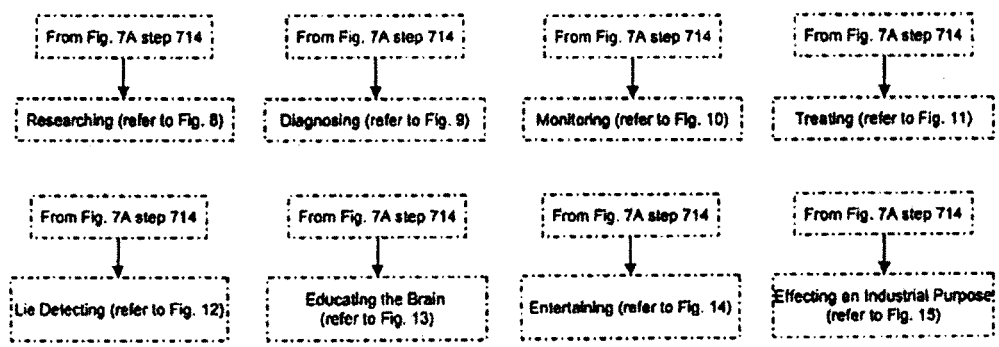
Figure 7B
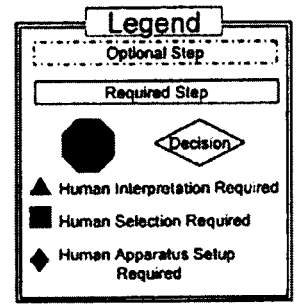

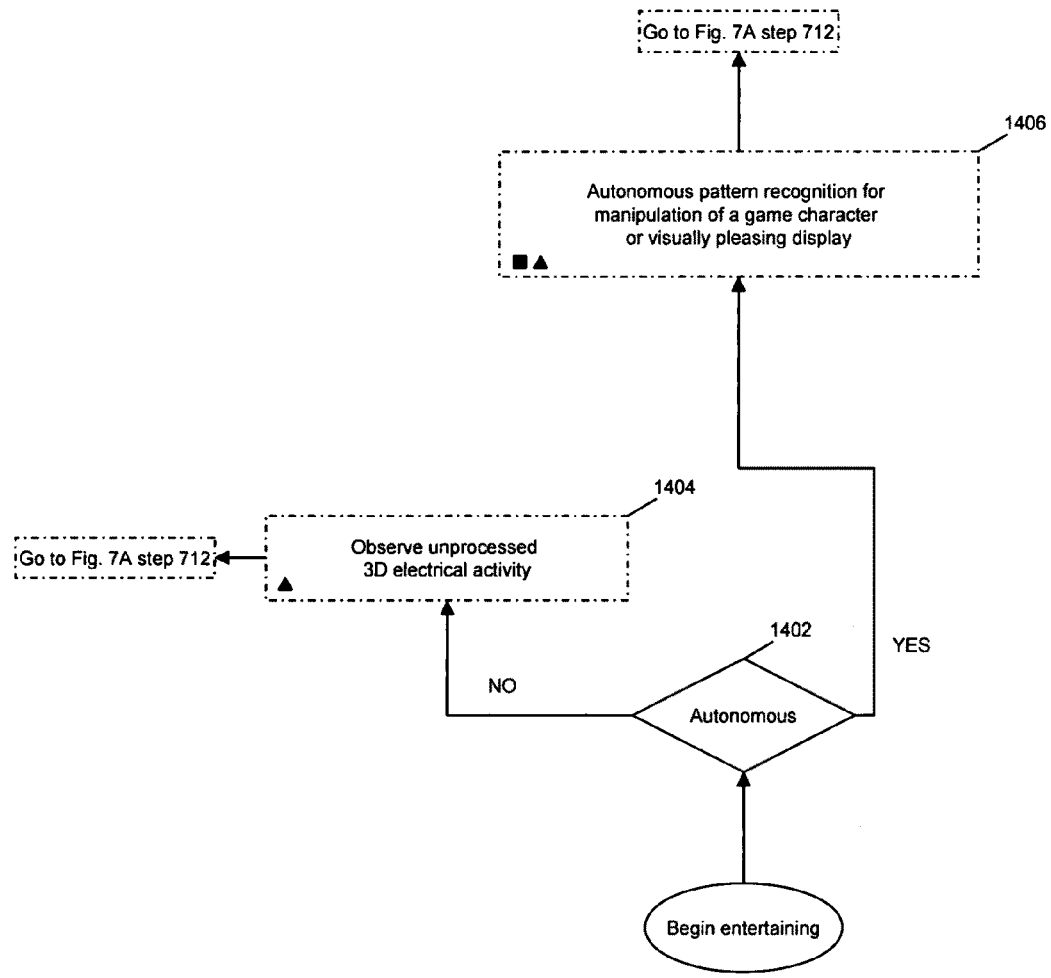
Figure 14
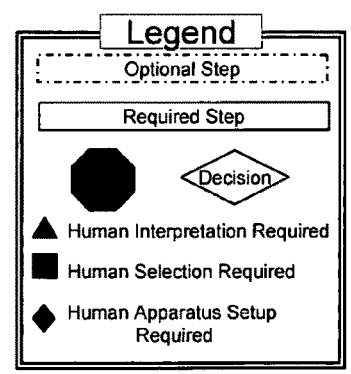

THREE-DIMENSIONAL LOCALIZATION, DISPLAY, RECORDING, AND ANALYSIS OF ELECTRICAL ACTIVITY IN THE CEREBRAL CORTEX

CROSS-REFERENCE TO RELATED APPLICATIONS

This application is a Continuation of PCT application PCT/CA20061000776 filed May 16, 2006, which claims priority to U.S. provisional patent application 60/681,140, filed 2005 May 16. This application claims priority to each of these applications and incorporates the content of each by reference.

FEDERALLY SPONSORED RESEARCH

Not applicable

SEQUENCE LISTING OR PROGRAM

None attached

BACKGROUND OF THE INVENTION

1. Field of Invention

The present invention relates largely to medical devices concerning the brain, and is a method and apparatus to non-invasively localize, in three dimensions (3D), electrical activity in the cerebral cortex of the brain, display the localized electrical activity in the form of 3D "motion pictures", and to perform statistical analysis and quantification of the localized electrical activity, all in near-real time.

2. Prior Art

The human cerebral cortex is the convoluted outer surface of the brain, commonly known as 'gray matter' and is responsible for many of the higher functions including those associated with thought, action, emotion and sensation. The cerebral cortex, largely due to its complexity, is also susceptible to a large number of disorders and diseases, many of which lack proper objective diagnoses, or require expensive medical equipment to properly diagnose.

Often, elucidating specific cortical functions or diagnosing diseases requires the three-dimensional (3D) localization of what regions of the cerebral cortex are responsible, and subsequent display of these regions in the form of one or more images. There are a number of existing technologies that have been utilized that accomplish this, including examples such as:

a. Magnetic Resonance Imaging (MRI) and Functional Magnetic Resonance Imaging (fMRI); U.S. Pat. No. 4,812,720 (1989)
b. Positron Emission Tomography (PET); U.S. Pat. No. 4,284,890 (1981)
c. Single Photon Emission Computed Tomography (SPECT); U.S. Pat. No. 4,584,478 (1986)
d. X-Ray Computed Tomography (CT); U.S. Pat. No. 3,922,552 (1975)
e. Magnetoencephalography (MEG); U.S. Pat. No. 4,591,787 (1986)

Each of these technologies has its strengths and weaknesses. Some of the technologies listed above are capable of localizing specific features to a resolution of less than 1 mm, although only MEG is capable of capturing many three-dimensional images per second at that resolution; the others require seconds to minutes for each image. MEG is also the most costly of the above technologies and the least accessible.

In general, these technologies are very expensive, typically $1,000,000-$10,000,000 USD per machine. In addition to the cost of the machine itself, technical staff, maintenance fees, specialized environments, and chemical or radioactive agents may also be required. For example, SPECT and PET scanners perform their function by detecting injected radioisotopes to obtain functional and/or spatial information; the sensitivity of MRI scanners can be increased by introducing chemical contrast agents into subjects; and MEG scanners require magnetically shielded rooms, often located underground. These machines are physically large and require entire spaces to be devoted to their function, hence restricted to larger medical institutions and universities, and most definitely not portable. It is primarily for the aforementioned reasons that these technologies are largely inaccessible to both members of the general population and much of the academic and private research community.

Consequently, there is a clear need for new technologies that can perform to a similar level, but for much-reduced base and operating costs, while increasing portability.

There exists, however, a related technology that can match the temporal resolution of MEG, is portable, but cannot localize in three dimensions events that take place within the cerebral cortex. The related technology, the electroencephalograph (EEG) recorder, can measure electrical potentials between any number of electrodes placed on a subject's scalp, and changes in the electrical activity of the cerebral cortex will produce a change in voltage, or electric potential, of the electrode. When the individually measured changes in voltage from an electrode are measured over time, it becomes a signal. The electrical activity of the cerebral cortex is thought to originate from the interactions between the firing (and resulting movement of ions) of excitatory pyramidal cells and inhibitory interneurons.

Attempts have been made within prior art to localize EEG signals and to elucidate the spatiotemporal patterns of electrical activity within the cerebral cortex, although there have been significant shortcomings in the results that these methodologies produce; for example, U.S. Pat. No. 4,407,299 to Culver (1983) restricts localization to a two-dimensional topographic map based on the known positions of the EEG electrodes but does not offer any depth information; U.S. Pat. No. 5,361,774 to Yamazaki requires prior knowledge of the function in question to generate an assumption by which the localization solution can refine; and U.S. Pat. No. 5,701,909 to Amir requires extensive computer processing due to solution-specific optimization which precludes widespread general use. U.S. Pat. No. 5,307,807 to Valdes Sosa (1994) describes a method and system to localize EEG signals in three dimensions, using an inverse solution approximation source localization algorithm, however it does not reduce to practice any applications, nor is it performed in near real-time, significantly reducing the clinical relevance, and it relies on tomographs (2D slices) to convey three-dimensional data, which complicates the interpretation of contiguous 3D data.

OBJECTS AND ADVANTAGES

Accordingly, several objects and advantages of the present invention are as follows:

it is an object of the invention to be used to localize electrical activity in the human cerebral cortex in three-dimensions;

it is an object of the invention to be used as an aid for diagnosis, and as an aid to medical monitoring and as an aid to treatment;

it is an object of the invention to be used as a research aid to investigate mental, psychological, and physical cortical processes, states, and/or conditions;

it is an object of the invention to be used in non-medical applications including entertainment, games, lie detection, industrial applications, peak performance training and educational purposes;

it is an object of the invention to display images of the localized electrical activity in 3D, in near-real time, in an intuitive manner in accordance with the interpretative ability and organization of the brains of the operators to understand the changing electrical activity in real-time 3D terms as opposed to 2D slices which are awkward to look at as seen with tomographic methods;

it is an object of the invention to record, display and analyze the localized electrical activity in various forms in near-real time: 1) transient, i.e. brief cortical activities (including events lasting less than a second); 2) cortical states which are longer activities; and 3) transitions from state to state or from event to event and between events and states;

it is an object of the invention to store the recorded localized electrical activity or original electrical signals to a recordable medium for later review;

the invention accomplishes the above all in near-real time with superior temporal resolution; conventional imaging modalities (with the exception of MEG) are not fast enough to capture fine details of many of events that occur in the cerebral cortex. Our invention also has the ability to detect events as short as permitted by the EEG amplifier utilized by the system; typically half a millisecond or less. The only other cortical imaging modality capable of this temporal resolution, MEG, is approximately 500 times more expensive than this setup and requires special magnetically shielded rooms;

the invention accomplishes the above in a computationally inexpensive manner, by incorporating the latest in inverse solution approximation source-localization algorithms. The algorithms mathematically reconstruct a three-dimensional electric activity distribution from a montage of EEG electrodes placed externally on the scalp. The algorithms have a spatial accuracy of approximately 7 mm or better, depending on which of the algorithms is utilized;

the invention can utilize many such algorithms, some of which have already attained extensive peer review, such as the LORETA, S-LORETA, and the Minimum Norm algorithms.

the invention accomplishes the above in a portable and inexpensive manner by avoiding the prohibitive operating and setup costs that render conventional cortical imaging modalities a inaccessible and by utilizing inexpensive EEG equipment coupled with a mobile computer running custom software;

the invention is practical, and can be used in an ordinary office setting and even potentially in an ambulance or in an operating room;

the invention is safe as it utilizes a type of hardware (EEG amplifiers and electrodes) that has been proven safe and has been in clinical use for several decades;

the invention can be used to make a rapid diagnosis as it operates in near-real time, which is of great practical use since a patient can potentially be diagnosed on the spot. This can potentially save lives as it could speed up implementing the correct treatment. In addition, in the absence of a rapid diagnosis, the delay leaves both doctor and patient alike wondering about the outcome;

the invention, by localizing EEG in 3D provides useful information about cortical activity that would otherwise be very difficult to find in the original EEG signals, due to the fact that signals from an electrode that when examined in isolation appear as "noise" because they are without spatial context. Localization provides a partial solution to the so called "signal to noise" problem which is a key challenge in the field and has been an impeding factor in developing EEG-based clinical diagnostic tests.

The objects of the present invention are useful and provides clear advantages over prior art for understanding how the brain works, for diagnosing and monitoring various neurological and psychological conditions, and as a guidance system for targeting parts of the brain for treatment interventions. For example, as much as 68% of the EEGs of psychiatric patients are abnormal, and there is a need for technologies that can localize the disturbed parts of the brain.

FURTHER OBJECTS AND ADVANTAGES OF THE INVENTION

Part of the value of the invention is derived from it being a near-real time modality but significant additional value originates from the analytical power created by its various data filters, three-dimensional display tools, statistical analysis tools and the graphical user interface, implemented within our software. By the term "graphical user interface" we mean our method of display and presenting images and visual information on the screen to the operator and not simply "still" two dimensional graphics. The invention displays evolving 3D images as they change with time on the screen.

The human cerebral cortex performs numerous functions and therefore it is not surprising that the devices and methods that image the cortex have a longer list of functions and uses than most inventions.

Diseases for which the Present Invention May by Utilized for Diagnosing, Monitoring and for Treating.

i. The present invention may be used as an aid to diagnose, aid to monitor and aid to treat a number of mental and behavioral disorders involving electrical abnormalities in the cerebral cortex, including diseases of the nervous system, medical conditions and psychological conditions.

ii. In many of the listed items below there are known abnormalities evident within the EEG and/or further QEEG (quantitative EEG, an extension of conventional EEG involving topographic maps) analyses. The methods of the present invention are such that they are designed to isolate spectral bands (specific frequencies or frequency ranges of EEG signals), vector temporal-spatial movement dynamics (changes in the direction and location of electrical flow) and to correlate the generator sources (putative sources of electrical activity within the cerebral cortex) in near-real time in three dimensions, thus identifying the locations and cortical electrical dynamics that underlie the EEG abnormalities. Regarding other items on the list below there are theoretical grounds for placing them here. The present invention is particularly suited for characterizing the abnormal electrical dynamics of many diseases involving the cerebral cortex. For all the conditions mentioned below that possess EEG abnormalities, it is possible to better characterize and localize them with the present invention. Diagnostic tests may be developed with the aid of clinical trials so as to create sets of normative data derived from normal individuals, and sets of data derived from diseased individuals which will be used for near-real time comparisons with data from a patient.

iii. The list below in this section includes not only the names of diseases and disorders but also the names of categories of diseases and disorders which have accepted definitions under the World Health Organization ICD10 system of nomenclature. This includes blocks F of the ICD10.

Block F: ICD-10 Chapter V: Mental and behavioural disorders

Accessible at: http://www3.who.int/icd/vol1htm2003/fr-icd.htm a) Organic, including symptomatic, mental disorders:

This includes Alzheimer's, vascular dementia, organic amnesic syndromes and other cortical dementias. There are examples in scientific literature showing electrical abnormalities in people with dementias. In Alzheimer's, increased low frequency activity (where activity is defined as higher EEG signal amplitude) and decreased mean frequency is often found within the EEG signals. In some dementias, the EEGs revealed increases in delta (1-3 Hz) and/or theta (4-7 Hz) power (where power is defined as the square of the EEG signal amplitude) and decreased mean frequency as well as decreased beta (12-35 Hz) power and dominant frequency in the occipital lobe. Since EEG has very little ability to localize these abnormalities, it is possible to better characterize them with the methods of the present invention as an aid to diagnosis, monitoring and treatment. Pick's Disease has EEG abnormalities which can be imaged and quantified in greater detail with the methods and apparatus of the present invention. Delirium Tremens has high frequency abnormalities on EEG.

b) Mental and behavioral disorders due to psychoactive substance use:

This includes substance abuse and drug-induced states affecting the cortex. This includes the stimulatory/depressive, toxic and withdrawal effects of psychoactive drug categories such as, but not limiting to, depressants, sedatives, stimulants, illegal narcotics, anti-epileptics, anxiolytics, sleep drugs, anti-psychotics, hallucinogens, anti-depressants, and inhalants; examples include, but are not limited to: cocaine, amphetamines, cannabis, caffeine, tobacco, nicotine, LSD, ecstasy, GHB, PCP, heroin, opium, hashish, mescaline, 'magic mushrooms', and alcohol. Studies of alcohol abuse have found increased beta activity, and alcohol intoxication studies have found decreased alpha activity and increased theta activity. We may build on these findings to make an improved test for alcohol intoxication. Increased alpha activity in frontal regions is associated with cannabis withdrawal and intoxication. Increased alpha and decreased delta activity is associated with crack cocaine withdrawal. The present invention may be used to determine their effects on the electromagnetic activities of the cortex which will be used to diagnose and plan the treatment of cortical states caused by these drugs.

c) Schizophrenia, schizotypal and delusional disorders:

In schizophrenia there is occasionally low mean alpha frequency as well as other alpha wave abnormalities or abnormalities of other frequency bands including frontal delta and theta excess on EEG.

d) Mood (affective) disorders:

Mood (affective) disorders include but not limited to unipolar and bipolar disorders including depression and mania. Alpha and theta wave abnormalities such as increased alpha and theta power are known to exist in unipolar depressed patients. Bipolar patients tend towards reduced alpha and beta activity.

e) Neurotic, stress-related and somatoform disorders:

Neurotic, stress-related and somatoform disorders include but are not limited to anxiety disorders, Obsessive Compulsive Disorder, reaction to severe stress, dissociative disorders, and somatoform disorders. Anxiety disorders often have reduced alpha activity.

f) Behavioral syndromes associated with physiological disturbances and physical factors:

This includes behavioral syndromes associated with physiological disturbances and physical factors including but not limited to anorexia nervosa, bulimia nervosa, non-organic sleep disorders including non-organic insomnia and non-organic hypersomnia, and non-organic disorder of the sleep-wake schedule, sleepwalking (somnambulism), sleep terrors, nightmares, and sexual dysfunction not caused by organic disorders or diseases.

g) Disorders of adult personality and behavior:

Disorders of adult personality and behavior include but are not limited to paranoid, schizoid, dissocial, emotionally unstable, histrionic, anakastic, anxious, dependant personality disorders as was as personality disorder unspecified types, and habit and impulse disorders including pathological gambling, gender identity disorders, disorders of sexual preference, psychological and behavioral disorders associate with sexual development and orientation h) Mental retardation:

Mental retardation includes mild, moderate, and severe forms.

i) Disorders of psychological development:

Disorders of psychological development including but not limited to specific developmental disorders of speech and language, specific developmental disorders of scholastic skills including developmental dyslexia, specific developmental disorder of motor function, mixed specific developmental disorders, pervasive developmental disorders including childhood autism and Rett's syndrome and Asperger's syndrome j) Behavioral and emotional disorders with onset usually occurring in childhood and adolescence:

These include hyperkinetic disorders, disturbances of activity and attention, conduct disorders, emotive disorders with onset specific to childhood, tic disorders including combined vocal and multiple motor tic disorder (de la Tourette)

k) Unspecified mental disorder:

Mental disorder, not otherwise specified.

iv. The list below in this section includes not only the names of diseases and disorders but also the names of categories of diseases and disorders which have accepted definitions under the World Health Organization ICD10 system of nomenclature. This includes blocks G of the ICD10.

Block G: ICD-10 Chapter VI: Diseases of the nervous system

Accessible at: http://www3.who.int/icdlvol1htm2003/fr-icd.htm a) Inflammatory diseases of the central nervous system:

This includes meningitis, encephalitis and abscesses.

b) Systemic atrophies primarily affecting the central nervous system.
c) Extrapyramidal and movement disorders:
   This includes Parkinson's Disease, and other diseases to the extent that they also involve the cerebral cortex.
d) Demyelinating diseases of the central nervous system:
   This includes multiple sclerosis.
e) Episodic and paroxysmal disorders:
   This includes the many forms of epilepsy, migraine, tension headache and other headache syndromes not limited to cluster, transient cerebral ischemic attacks and related syndromes including Amaurosis fugax, vascular syndromes of brain in cerebrovascular diseases, sleep disorders including disorders of initiating and maintaining sleep (insomnias), disorders of excessive somnolence (hypersomnias), disruptions in circadian rhythm including jet lag, sleep apnea, narcolepsy and cataplexy. In cerebralvascular disease slowing of EEG frequencies is highly correlated with decreased regional blood flow. Cerebralvascular diseases include strokes, suspected strokes or transient ischemic attacks.
f) Nerve and nerve root plexus disorders.
g) Polyneuropathies and other disorders of the peripheral nervous system.
h) Cerebral palsy and other paralytic syndromes:
   These include infantile cerebral palsy, hemiplegia, paraplegia and triplegia where the cause is cortical in origin.
i) Other disorders of the nervous system:
   These include hydrocephalus, toxic encephalopathy, cerebral cysts, anoxic brain damage, benign intracranial hypertension, postviral fatigue syndrome, encephalopathy, unspecified compression of the brain, cerebral edema, and Reye's syndrome.

v. Other diseases and disorders involving the cerebral cortex including many that are that are not explicitly mentioned in the above lists:
a) Disorders of belief and belief formation:
   This includes delusions and delusional states. Delusional states have in some cases been found to involve low frequencies on the EEG.
b) Cortical sensory disorders:
   This includes visual (such as cortical blindness and visual agnosia), acoustic (such as cortical deafness and auditory agnosia), tactile, smell (such as anosmia), vestibular (such as vertigo) and visceral sensory disorders (including irritable bowel syndrome and interstitial cystitis)
c) Other forms of cortical damage:
   This includes damage caused by stroke or brain injury. It is possible to localize this damage using indicators of reduced cortical function in the damaged areas using the present invention. Head injuries have been associated in the medical literature with increased theta power, decreased delta power, decreased alpha power, low coherence and increased asymmetry across the hemispheres of the brain. These abnormalities can be localized and better characterized using the present invention so as to provide diagnostic tests for the nature and severity of the injuries.
d) Other space occupying lesions:
   This includes brain tumors and cysts that will likely have regions of reduced activity.
e) Chronic pain:
   This may involve using the present invention to measure cortical areas such as the anterior cingulate gyrus. Chronic pain includes muscular and non-muscular pain, neuropathic pain, fibromyalgia and myofascial pain syndrome.
f) Specific learning disorders:
   These are disorders of the ability to acquire knowledge and some specific disorders have been associated with excess theta or decreased alpha and/or beta powers.
g) Disorders involving thought, feeling or combinations of the two:
   These include disorders of planning and foresight as well as of sentiments involving a combination of a thought and a feeling such guilt over an error, or the feeling of pride in an achievement.
h) Memory disorders:
   This includes disorders of memory storage and memory retrieval.
i) Reasoning disorders:
   This includes disturbances of making logical inferences.
j) Evaluative disorders:
   This includes disorders involving the formation of evaluative judgments as to what the person deems to be good or bad.
k) Disorders of comprehension and understanding such as agnosia.
l) Disorders of the self and the self-image:
   This includes disorder in self-representation and disorders of identity.
m) Other circadian disorders affecting the cortex.
n) Other movement disorders. This includes essential tremor and restless leg syndrome.
o) Social and conduct disorders.
p) Other psychosomatic illnesses.
q) Other speech and communication disorders.
r) Impulse control disorders.
s) Post Traumatic Stress Disorder.
t) Brain death.
u) Truth disorders:
   This includes any disorder in the brain of assigning an idea to the category of being true or untrue.

Disease-Related Uses as an Aid to Near-Real Time Monitoring:

Disease-related monitoring refers to ongoing measurement and imaging which detects changes in the brain. Whereas diagnosis aims to determine the nature a disorder, monitoring is useful to determine changes including deteriorations or improvements in a condition. Medical monitoring is especially useful in observing patients who are unstable or vulnerable.

The medical monitoring uses of the present invention include:
a) Near-real time monitoring applied to any person with a medical or psychological disorder involving the cerebral cortex including any of the conditions listed above in section [00026].
b) Near-real time monitoring of surgical patients who are under general anesthesia for adequacy of anesthesia and cortical disturbances erupting while unconscious. The present invention may be integrated with alarm systems to provide early notification of medical personnel of any deterioration.
c) Near-real time monitoring of neurology patients and neurosurgery patients in the hospital, such as coma patients, for improvements or deteriorations so as to position the doctor to administer an intervention.

d) Near-real time ambulatory monitoring and remote monitoring of critically ill persons such as acute head trauma patients that are inside an ambulance or at remote locations. This is useful in detecting intermittent symptoms and events including dizziness or symptoms of seizures.
e) Monitoring the change in a person's state or condition by continuous monitoring before, during and after exposure to a stimulus such as a sensory stimulus, with or without the help of a stimulator.

Disease-Related Uses as an Aid Treatment.

a) To aid in prosthetic treatment such as aiding individuals with peripheral nerve damage, such as amputees. This may be performed by utilizing the present invention to serve as part of a brain computer interface (BCI) whereby signals emanating from the patient's brain are harnessed in order to help the patient to control the movements of the patient's prosthetic device or the patient's own muscles.
b) Near-real time treatment may applied to any person with a medical or psychological disorder involving the cerebral cortex including any of the conditions listed above in section [00026].
c) To aid in treatment by using the present invention as a guidance system to direct the use of external stimulators including transcranial magnetic stimulators so that they can favorably be directed towards specific target areas in the brain, or to guide the application of implantable brain stimulators or inhibitors.
d) To aid in treatment serving as a method for biofeedback treatment whereby the patient is presented near-real time images of his/her brain's own electrical activity to enable him/her to attempt to favorably alter the underlying signals.

As an Aid to Researching Mental, Psychological and Physical Cortical Processes and States.

The techniques and methods described herein may be used for medical research and brain physiological research to understand the causes of diseases, human behavior, and mental processing. Research applications of the present invention include:

a) As an aid in the characterization of normal mental processes and normal physiological events and states.
b) Research into neural pathways and the discovery and further elucidation of migratory patterns of cortical electrical activity.
c) As a tool to help interpret EEG recordings of normal and abnormal mental activity by revealing the sites of generators in the brain and the angular movements of electrical fields that contribute to EEG waveforms.
d) As an aid in the understanding of the translational and rotational movement of electrical fields produced by the brain.
e) As an aid in the recognition of functional elements of the brain, i.e. areas of the brain that work together to help perform a particular mental function.
f) As an aid in the characterization of a number of brain disorders, conditions, and states such as those listed in section 00026-00028 so that effective diagnoses, monitoring methods and treatments can be developed.
g) As an aid in the characterization of:
  i. thoughts and ideas,
  ii. feelings and emotions,
  iii. beliefs,
  iv. sensations,
  v. learning,
  vi. understanding and comprehension,
  vii. reasoning,
  viii. desiring and motivation,
  ix. memory,
  x. evaluative processing, (including processing of pleasure and pain)
  xi. truth processing,
  xii. planning,
  xiii. judgment,
  xiv. movement processing,
  xv. speech and communication,
  xvi. representation, including self-representation,
  xvii. predispositions
  xviii. planning.
h) To serve as an aid in the process of drug development by helping determine the areas of the cerebral cortex where the electrical activity is affected by experimental and established pharmaceuticals, hence providing insight on the locations and mechanisms of action of these drugs.

Non-Medical Applications Including Industrial Applications, Entertainment, Games, Lie-Detection and Education.

Applications of the present invention may include the above-mentioned non-medical applications for the following reasons:

a) Entertainment: It is fascinating to look at cortical activity in near-real time, hence the present invention has entertainment value. It is an object of the present invention to use it as a method of entertainment by allowing a person to observe his/her own electrocortical activity or that of other people in near-real time 3D. This includes using it as a game in which the user tries to alter the user's cortical images on the screen, which in a more complex implementation leads to the point below.
b) Activation of external effectors using a brain-computer interface (BCI): It is possible to isolate a portion of the localized electrical activity of the cortex and to use a computer to recognize certain patterns and then to use those patterns to activate an external effector, i.e. a mechanical device which is arranged so as to have a tangible effect on objects in the surrounding environment. Examples include industrial processes to control an external mechanical device, such as an assembly arm, or other industrial robots.
c) As an educational tool: It is possible to educate people to modulate their cortical activity by using the images on the screen as a form of biofeedback so as to teach the brain to work more effectively. EEG methods exist to do peak performance training. It is possible to improve on these techniques using the present invention.
d) As a method of determining if a person is telling the truth or lying. Signature images and signature data patterns for lying and truthfulness may be identified through research trials utilizing the present invention. The trials may involve measuring people who are instructed to lie or instructed to tell the truth and who comply with this request while having their brain electrical activity recorded. The trial may also be conducted on people who actually lie when the person administering the test does not know during the testing session that the test subject is lying; this will capture cortical activity during actual lies. These two trials will provide a dataset of electrical activity of lying versus truthfulness and this dataset will later be used when testing future subjects for lying and will serve as a means for comparison. It is possible to apply near-real time tools described in the present in the technical specifications of this document to isolate the signals indicative of lying from other signals coming from the test subject's brain that are unrelated to lying. Near-real time activity emanating from the subject's brain may be displayed on a monitor for live visual analysis by the mind of the examiner. A conclusion that a patient has lied can be drawn if the examiner observes the near-real time display of a signature pattern for lying that is present in the data base. Or alternatively, it is possible to use the tools for near-real time statistical analysis described in this document to aid the examiner in identifying a lie.

SUMMARY OF THE INVENTION

The present invention describes a method and apparatus to localize the electrical signals in measured from a subject's scalp surface, in near-real time and to generate dynamic three-dimensional information of the electrical activity occurring within the cerebral cortex of the brain. It can produce images that can be immediately inspected and analyzed by an operator in near-real time, resulting in a powerful new cortical imaging modality, which we denote as Dynamic Electrocortical Imaging (DECI). The present invention involves the use of a computer, an electroencephalographic (EEG) amplifier, EEG electrodes, and custom software. It can measure healthy and diseased cortical events and states in both conscious and unconscious subjects. This is useful, as it allows for the diagnosis, monitoring and treatment of cortical disorders, while also furthering the understanding of the human brain and lending use to additional non-medical applications such as in entertainment, education, lie-detection and industry. We have implemented the methods of the invention using software, written by us, in conjunction with readily available EEG hardware. Furthermore, we can apply this same method to pre-existing data and when doing so, EEG hardware is not required. By having a practical near-real time 3D imaging system, we hope to bring a far more accessible technology to doctors, researchers, individuals, and private clinics to better diagnose, monitor, treat and understand many of the conditions and abnormalities of the brain.

BRIEF DESCRIPTION OF THE DRAWINGS

The invention may be more completely understood in consideration of the following detailed description of various embodiments of the present invention in connection with the accompanying drawings, in which:

FIG. 2 depicts the mathematical transformation of electrical signals received by the electrodes into 3D localized electrical activity data using an inverse solution approximation.

FIG. 14 depicts a flowchart which is an extension of FIG. 7 whereby a human operator has decided to utilize the present invention for the purpose of entertaining.

DETAILED DESCRIPTION OF THE INVENTION

Figure 1:
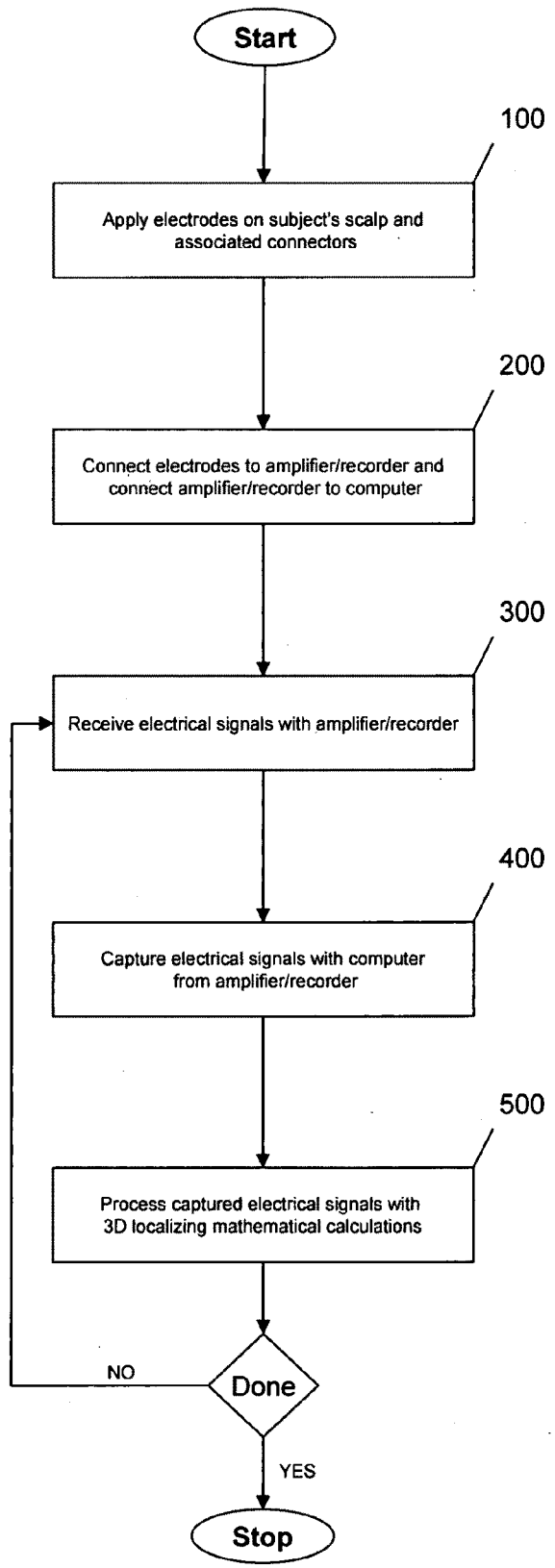
FIG. 1 depicts a flowchart outlining the process of setting up, recording, capturing and localizing cortical electrical activity in near-real time by the present invention.

A Preferred Embodiment of the Present Invention—FIG. 1

A preferred embodiment of the present invention is outlined in FIG. 1. It consists of several fundamental steps where:

Step 100 entails the application of electrodes on a subject's scalp. This requires a practical method to hold the electrodes in place on the scalp so as to make good electrical contact. Typically this is accomplished with manually attached electrodes with adhesives or caps/cap-like structures that fit over a subject's scalp that integrate or have adapters for the electrodes; a number of these are commercially available. A conductive medium is also generally required for the conductance of electrical signals between the scalp and electrodes; typically the conductive medium is the same as the adhesive used, although it can be separate. The positions of the electrodes may be known to assist in the localization calculations, or generalized electrode positions based on ratios or morphological features of the scalp, such as the 10-20 System, may be utilized. The electrodes may also be placed symmetrically, or asymmetrically, around the subject's head and different caps with varying numbers of electrodes and electrode spacing may also be utilized. Custom electrodes may also be utilized with varying geometrical shapes and configurations.

Step 200 entails the connecting of the electrodes to the EEG amplifier/recorder that digitizes signals obtained from electrodes placed on a subject's scalp. The particular setup used in the demonstrated reduction to practice includes a Twente Medical Systems International (TMSI) REFA32 digital EEG recorder.

Step 300 entails the receiving of electrical signals from the subject by the EEG amplifier/recorder.

Step 400 entails the capturing of relevant electrical signals by a computer, from the EEG amplifier/recorder. This is a multi-step process as the signal that is output by the amplifier/recorder is unusable in its raw state. It is at this point data may be subjected to near real-time component and feature isolation and artifact (noise) removal, such as those generated by movement, interfering electric fields, and what is known as the 'DC-offset' (the potential difference, or voltage, resulting from the interface between scalp and electrode which is far larger in magnitude than any of the relevant electrophysiological signals). The filters may include, but are not limited to; low, high, band-pass, or band-stop filtering, discrete Fourier analysis, Kalmann filtering, Z or Hilbert transforms, or similar analytical filtering or spectral analysis techniques known to those skilled in the art. For example, DC-offset would be removed using a frequency filter such as the Fast Fourier Transform (FFT), or windowed sinc filter to remove all very low frequencies, typically below 0.1 Hz. EEG data filters generally operate by transforming the most recently acquired EEG signal (or frames, where the number of frames acquired per second is equal to the sampling frequency of the EEG amplifier/recorder) by a process specific to the particular filter in question; for example, the windowed sinc filter, designed to isolate or remove a range of frequencies would involve convolving the most recent segment of EEG frames acquired from the recorder with the filter kernel (generated from the specified parameters of high and low ends of a frequency range along with the intention to band-pass or band-stop those frequencies). It is noted that DC-offset removal may not be required if another filter operates on the data such that the removal would be superfluous; an example of this would be a band-pass filter between 8 and 12 Hz, as all <0.1 Hz frequencies would be removed inherently. It is also during this step that the electrical signals (either pre- or post-filtering) may be recorded to random access memory, onto an external media such as a CD, DVD or cassette, or onto a hard drive. The particular setup used in the demonstrated reduction to practice includes an Intel Pentium IV-2.4 GHz desktop computer with 1 GB of RAM. The software utilized by the demonstrated reduction to practice is designed in a way that multiple filters can run in tandem on the same set of data, and the filters exist as dynamic linked libraries such that they can be expanded and upgraded independently of the main program (hereafter defined as plugin architecture); the software can also record pre- and post-filtered electrical signals to random access memory, hard disk, or both.

Step 500 entails the use of a computer in processing the captured electrical signals from step 400, transforming it into localized electrical activity represented within three-dimensional space using a mathematical procedure, or combination of procedures. FIG. 2 expands on this step when using inverse solution approximation algorithms for localization. At this point, the localized electrical activity data can optionally be filtered, e.g. for statistics, near-real time diagnostics, state changes. This also utilizes plugin architecture. After the transformation, the data can optionally be displayed on a monitor in near-real time.

Near-real time recording and 3D localization of electrical activity is accomplished by the continuous capture and processing of EEG data (steps 300-500; a loop of operation) until the termination of the procedure.

Localization of Electrical Activity Utilizing an Inverse Solution Approximation—FIG. 2

FIG. 2 depicts the transformation of electrical signals captured and processed by the computer, from the EEG amplifier/recorder into a 3D solution space utilizing an inverse solution approximation. The inverse solution approximation involves a transformation matrix that converts electrical signals into localized electrical activity confined to a solution space, representing the volume and shape of the cerebral cortex. Localization is accomplished by multiplication of each new frame of captured EEG data (E) by a transformation matrix (T) that is generated by the inverse solution approximation algorithm in use to yield the array of voxels containing localized electrical activity (V). Voxels are defined as discrete units of volume within the solution space and they contain the localized electrical activity for that particular region of the cerebral cortex. The localized electrical activity for each voxel is represented as a three-dimensional vector with an x, y and z component. The demonstrated reduction to practice currently implements the inverse solution approximation algorithm known as LORETA, details of which can be found in:

Pascual-Marqui R D, Michel C M, Lehmann D. Low resolution electromagnetic tomography: a new method for localizing electrical activity in the brain. International Journal of Psychophysiology 1994, 18:49-65.

Any appropriate inverse solution approximation algorithm could be used; other possibilities include but are not limited to:
  i) L2 minimum norm inverse solution:
    Hamalainen M S, Ilmoniemi R J (1984): Interpreting measured magnetic fields of the brain: estimates of current distributions. Technical Report TKK-F-A559. Helsinki: Helsinki University of Technology.
  ii) L1 minimum norm, also known as the selective minimum norm, inverse solution:
    Matsuura K, Okabe Y (1995): Selective minimum-norm solution of the biomagnetic inverse problem. IEEE Trans Biomed Eng 42: 608-615.
  iii) Backus and Gilbert method:
    Backus G, Gilbert F (1968): The resolving power of gross earth data. Geophys J R Astron Soc 16:169-205.
    Grave de Peralta Menendez R, Gonzalez Andino S L (1999): Backus and Gilbert method for vector fields. Hum Brain Mapp 7:161-165.
  iv) Location-wise Normalized Weighted Minimum Norm:
    Fuchs M, Wagner M, Kastner J. Boundary element method volume conductor models for EEG source reconstruction. Clin Neurophysiol 2001; 112:1400-7.
  v) LAURA (Local Auto-Regressive Averages):
    Andino S. Electrical neuroimaging based on biophysical constraints. Neuroimage 2004; 21:527-39.
  vi) s-LORETA (Standardized low resolution brain electromagnetic tomography):
    R. D. Pascual-Marqui, Standardized low resolution brain electromagnetic tomography (sLORETA): technical details. Methods & Findings in Experimental & Clinical Pharmacolgoy 2002, 24D:5-12. Author's version, details of which can be found at http://www.unizh.ch/keyinst/NewLORETA/QuoteLORETA/QuoteLORETA.htm
  vii) Standardized shrinking LORETA-FOCUSS:
    Liu H, Schimpf P H, Dong G, Gao X, Yang F, Gao S IEEE Trans Biomed Eng. 2005 October; 52(10): 1681-91. Standardized shrinking LORETA-FOCUSS (SSLOFO): a new algorithm for spatio-temporal EEG source reconstruction.

The demonstrated reduction to practice also currently implements a solution space of 2394 voxels available in the public domain, based on the MNI-305 template of neuroanatomical data from the Montreal Neurological Institute (MNI), based on the averaging of 305 MRI scans of human brains. This solution space is first described in:

A. C. Evans and D. L. Collins and S. R. Mills and E. D. Brown and R. L. Kelly and T. M. Peters, "3D statistical neuroanatomical models from 305 MRI volumes", Proc. IEEE-Nuclear Science Symposium and Medical Imaging Conference, 1813-1817, 1993.

Any appropriate cortical solution space could be used; other possibilities include but are not limited to:
  a) The International Consortium for Brain Mapping 152 Brain Average (ICBM152): Evans, A. C., Collins, D. L., et al., Three-dimensional correlative imaging: applications in Human brain mapping. In: Huerta, M. (Ed.), Functional Neuroimaging: Technical Foundations. Academic Press, San Diego, pp. 145-162, 1994.
  b) Talairach space:
    Talairach, J., Tournoux, P., Co-Planar Stereotaxic Atlas of the Human Brain. Thieme, New York, 1988
  c) The pediatric solution space in development at the Pediatric Data Center at the MNI
  d) An individualized solution space derived from a subject's own MRI or CT scan.

The basic display result using the MNI 305 solution space is demonstrated in FIG. 5A.

Figure 3:
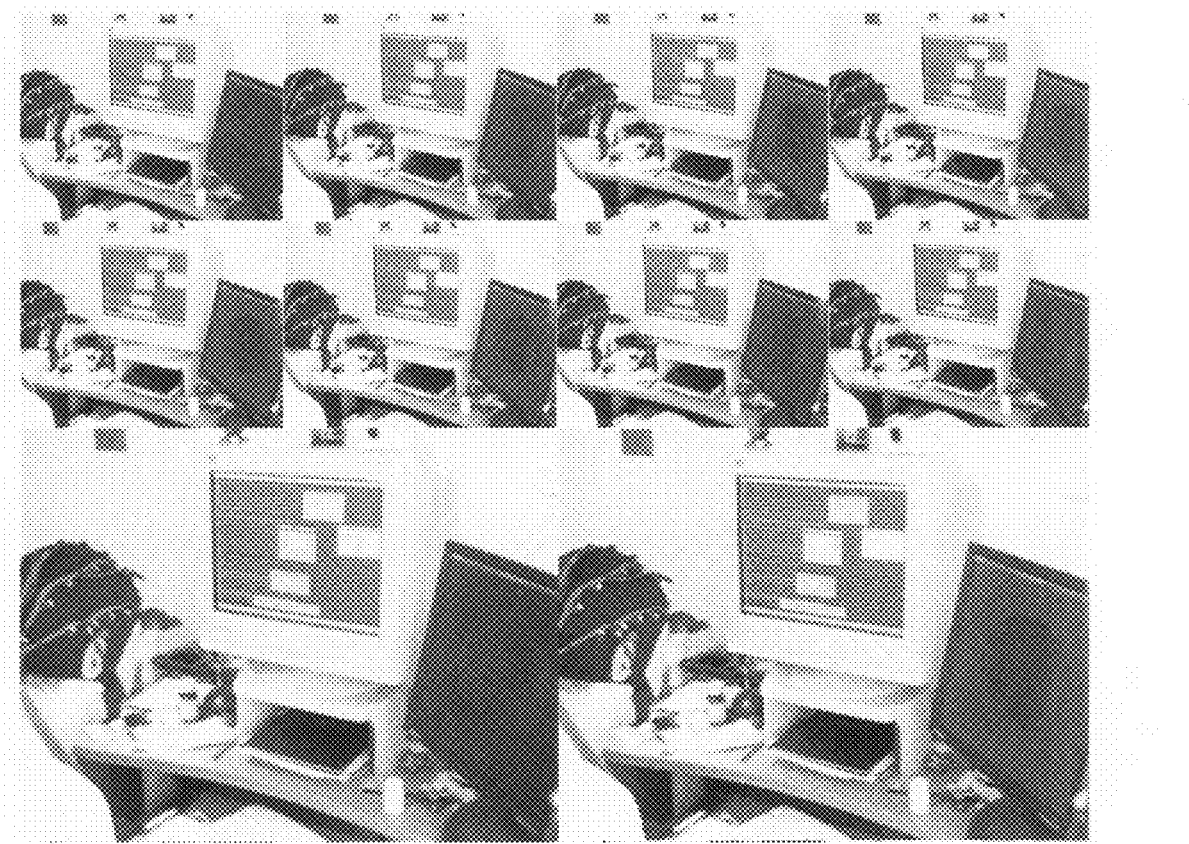
FIG. 3 depicts a series of consecutive frames within a movie demonstrating the first successful application of the present invention in near-real time.

First Successful Reduction to Practice of the Present Invention—FIG. 3

FIG. 3 depicts the first successful reduction to practice of the present invention. The hardware utilized at the time was the TMSI REFA32 digital EEG recorder connected to a 19 electrode (+1 ground) NeuroScan cap, and an Intel Pentium IV-2.4 GHz desktop computer with 1 GB of RAM, although we have later successfully included the use of 32(+1 ground) MedCat silver chloride (AgCl) sintered ring electrodes. The demonstrated reduction to practice utilizes custom-written software by the inventors. The software written to implement the methods of this invention is designed to:
  a. Display both near-real time and pre-recorded data using three-dimensional cubes (known as voxels) projected onto a two-dimensional display surface (i.e. the screen), and can freely be manipulated in ways that allow for the visualization of any region, whether on the surface or buried within the rest of the grey matter. This is true three-dimensional near-real time manipulation of the cortex.
  b. Use the OpenGL library to display the three-dimensional graphics, although other three-dimensional application programming interfaces may be supported in the future.
  c. Be programmed in C++ and speed-optimized to allow fast user responsiveness and the execution of many potential data filters and display windows.
  d. Display multiple windows corresponding to different points of view of the cortex (vantage points), display options, or sets of data filters.
  e. Handle far larger data-sets than similar non-real-time methods found in prior art; the amount of data that can be analyzed is solely limited by the amount of memory of the computer the analysis is performed on.
  f. Run on any computer that can run Microsoft Windows™, although the responsiveness is dependant on both the speed of the video card and microprocessor within the computer; other operating systems may be supported in the future.
  g. Be intuitive and easy to use, extending its accessibility to individuals without developed computer skills.

Methods of Near-Real Time Manipulations of Localized Electrical Activity—FIGS. 4-6

FIGS. 4-6 depict three groups of tools that allow the human operator to manipulate and display localized electrical activity within the solution space comprised of voxels. They are a selection of independent tools whose use is not required for the function of the present invention; they serve to facilitate analysis and interpretation. These tools may be utilized alone or in any combination.

Group 1: Tools to Manipulate the Graphical Display and Analysis of Voxels—FIG. 4

FIG. 4 depicts diagrams that demonstrate the various ways by which the voxels that comprise the solution space can be displayed. Generally, each voxel within the solution space utilized is displayed using 3D graphics, as a discrete cube (6 sided polygons) within each voxel's own assigned position as determined by the solution space model used. Each solution space may be given its own display window, or superimposed onto an existing window.

Figure 4A:
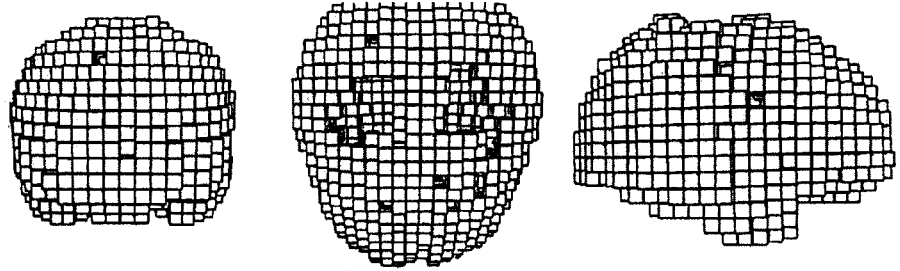
FIG. 4 depicts the variety of methods by which voxels can be graphically displayed.

FIG. 4A depicts the solution space comprised of voxels in three points of view, drawn as a 3D array of cubes; front (left), top (middle), and right (right) views.

Figure 4B:
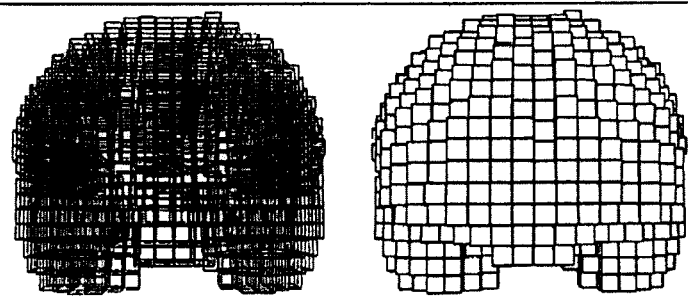

FIG. 4B depicts the tool for near-real time translucent visualization of displayed voxels; on the left is the solution space with the tool enabled, whereas the solution space on the right has the tool disabled. The purpose of this tool is to allow the operator to visualize activity occurring at all depths. This is useful for viewing the entire cortex at a glance, as it will reveal all inner activity with the same weighting as any surface activity, and instantly reveal any significant deeper signals. This is achieved by means of drawing all voxels with additive blending, that is, instead of replacing the pre-existing pixels of the 2D projection plane (i.e. the screen) of the 3D solution space (that is subsequently rendered to the screen), we add the pixel values of the current object drawn closer to the viewing plane to the pre-existing pixels. For example, if there was a voxel with a value of 100, and we drew a new voxel that would partially or completely occlude the underlying voxel, with a value of 50, the resulting area where the two voxels overlap would have a value of 150. If additive blending was not used that area would have a value of 50, and the new voxel would have partially or completely replaced the color value of the deeper voxel depending on the spatial arrangement of the two voxels.

Figure 4C:
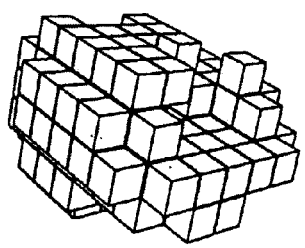

FIG. 4C depicts the tool for near-real time spatially filtered data on the basis of regions of interest (ROI). This is useful in such applications as when the operator is interested in only one region of the cortex. Such areas may be deep inside the cortex thus making it desirable to filter out regions that are not of interest while the near-real time display or analysis is being generated. We achieved ROI filtration by implementing a spatial filter that takes a single 3D coordinate selected by the user and then only processes those voxels that are within the spherical boundary defined by the user as a radius from that central coordinate.

Figure 4D:
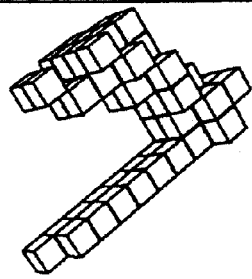

FIG. 4D depicts the tool for near-real time spatially filtered data on the basis of neuroanatomical information. This is useful as there is a massive amount of scientific literature on the subject of what is called functional localization, with a great deal known about the function of many regions of the brain. There is a need in research and in clinical work to be able to focus on a region of interest, so as to be able to later correlate findings made by imaging or analysis with what is known about a particular neuroanatomical region. We achieved this spatial filtering by assigning each voxel multiple description fields by which they could be identified as being part of a series of neuroanatomical regions, and then only displaying those voxels that are members of the neuroanatomical region in question. In the implementation demonstrated, the neuroanatomical classifications of each voxel originate from a table generated by the Montreal Neurological Institute based on the solution space currently utilized by the software and described previously (MNI-305).

Figure 4E:
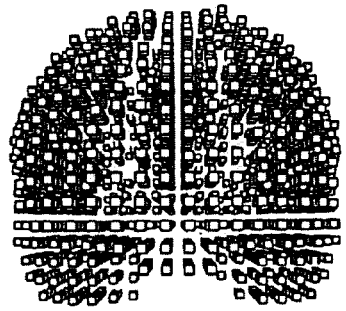

FIG. 4E depicts the tool to control the display of voxel size. This enables reductions in voxel size to allow for visualization of buried features. This is useful when looking at 3D images the cortex and when it is desirable to look at underlying voxels while preserving their colorimetric values that may be lost using other tools (e.g. the translucent visualization tool). This method essentially shrinks the displayed size of each voxel, effectively creating gaps in between the voxels, allowing for the visualization of deeper voxels. We achieved this by adding a scale parameter s within the voxel drawing function that draws 3D cubes of a length, width, and height of the standard voxel size, v*s. The variable s, unless otherwise specified by this tool has a value of one (1).

Figure 4F:
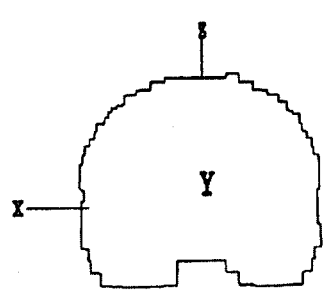

FIG. 4F depicts the tool for visualization of voxel outlines in a disabled state, since this tool is especially useful in delineating the boundaries between individual voxels as can clearly be seen in every figure of this section. This was achieved by drawing a series of 12 lines, forming a wireframe cube of a slightly larger size than the solid polygons comprising the voxels. The X, Y and Z axes, further described in FIG. 6E, are labeled in this figure to orient the reader.

Figure 4G:
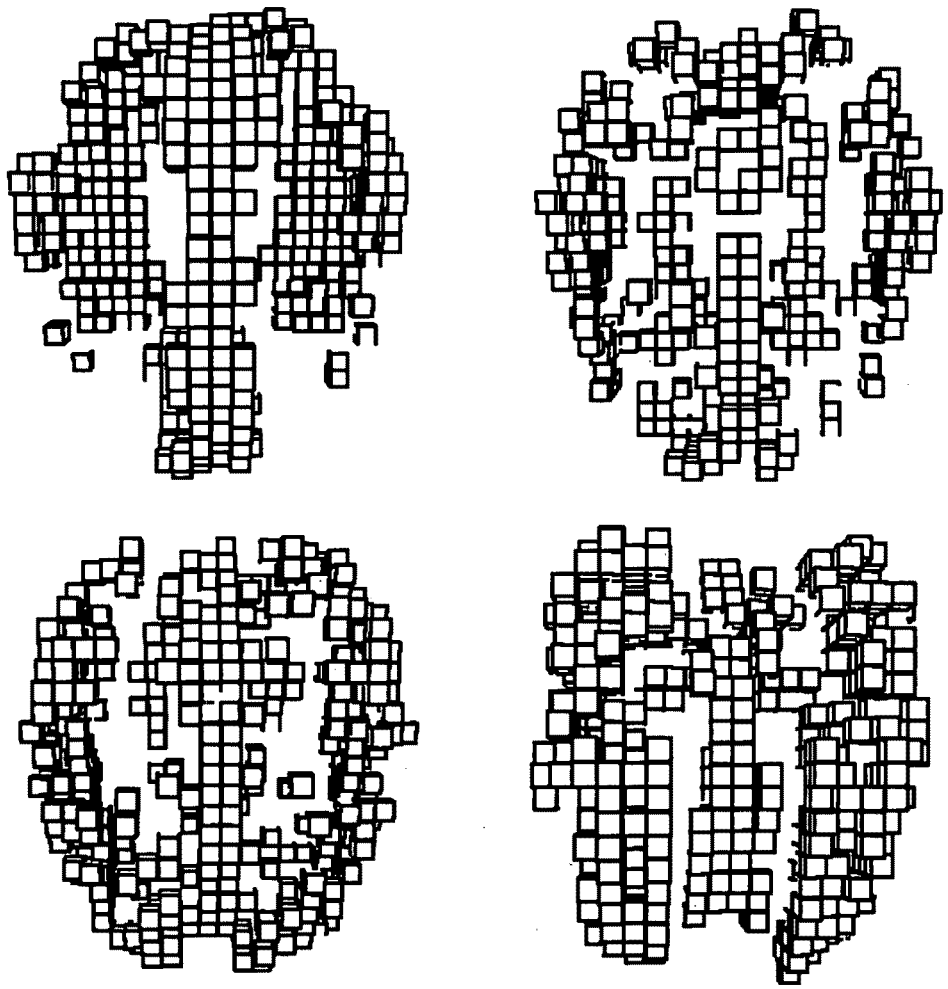

FIG. 4G depicts the tool for the near-real time selective display of cortical shells to view buried visual features. This is useful for removing surface features that may otherwise occlude the visualization of significant events deeper within the cortex. We achieve this by means of assigning each voxel within the solution space a shell number, of an integer type, based on its distance from the center of the solution space. Only those voxels that have a shell number matching the range of shells to be displayed are then displayed on the screen. The demonstrated implementation of this tool divides the cortex into five distinct shells.

Group 2: Tools to Analyze and Graphically Display Localized Electrical Activity—FIG. 5

FIG. 5 depicts diagrams that demonstrate the various ways by which the electrical activity within each voxel can be represented graphically. As mentioned in FIG. 2, the inverse solution approximation algorithms output 3 values for each voxel of the solution space, for each given instance in time; an x-component (x), a y-component (y), and a z-component (z) of a vector indicating the amount (magnitude) of electrical activity and a direction in which this electric activity is moving. Generally, there are two approaches to represent this electrical activity; displaying within each voxel, the magnitude (m; defined as the square root of the sum of the components squared; $m=\sqrt{(x^2+y^2+z^2)}$) of the electrical activity vector (defined as current density) of that voxel as a shade of color, increasing in intensity as electrical activity increases; and secondly, displaying the magnitude and direction of the electrical activity vector as a line with a distinct direction and magnitude emanating from the center of each voxel.

FIG. 5A depicts the electrical activity of each voxel within the entire solution space as shades of color. This represents the magnitude, or amount, of electrical activities occurring within the solution space. FIG. 5C depicts the first 54 voxels of the solution space, represented in the same way, for increased clarity. This essentially represents the amount of each current density in each voxel as the color of the voxel. This is useful as the operator needs a convenient method of continuously visualizing the level of electrical activity in a voxel or a set of voxels without having to resort to looking at tables and numbers from which these activity levels are internally derived. This is also very useful as a shortcut to help the viewer to recognize such patterns as "hot spots" of high activity and hot clusters, cold spots and cold clusters and current density gradients from one voxel to another. We achieved this by multiplying the value of the current density at each instant by a user-adjustable scalar (referred herein as the display gain) that is then used as a parameter by the voxel drawing function to determine its displayed color. In the current implementation reduced to practice, a bright blue shade indicates high levels of electrical activity, and darker blue shades, lower levels; other single color shades or false-color spectra are easily possible.

FIG. 5B depicts the electrical activity of each voxel within the entire solution space as a combination of shades of colors and lines. The lines represent both the magnitude and direction of the electrical activities within the solution space while the shades represent only the magnitude, as shown in FIGS. 5A and 5C. The lines protruding from the voxels shown in FIG. 5B directly represent the vectors of electrical activity. FIG. 5D depicts the first 54 voxels of the solution space, represented in the same way, for increased clarity. We achieved this by drawing a line from the center of the voxel (c) to the center of the voxel plus the voxel's electrical activity vector (v) multiplied by a scalar (s) (referred herein as the vector gain); in symbolic form this means drawing a line from c to c+v*s. There are several ways to further display these vectors of electrical activity. In the current implementation reduced to practice, the vector is drawn in white.

FIG. 5E depicts the electrical activity vectors as two-tailed entities for purposes such as the facilitation of the correlation between voxels and their nearby electrode positions. This is accomplished by drawing a second line from c to c−v*s for each voxel. In this drawing, the thicker lines represent vectors in the opposite direction to the electrical activity while the thinner lines represent the true vectors; in addition, only the first 54 voxels of the solution space are represented for increased clarity. In the current implementation reduced to practice, the true vector is drawn in red, while the negative vector is drawn in blue.

FIG. 5F depicts only the directional (angular) information of the electrical activity vectors in the first 54 voxels of the solution space. This is accomplished by normalizing each vector to a length of one by dividing each vector component by the magnitude of the vector; x'=x/m, y'=y/m, z'=z/m.

Figure 5G:
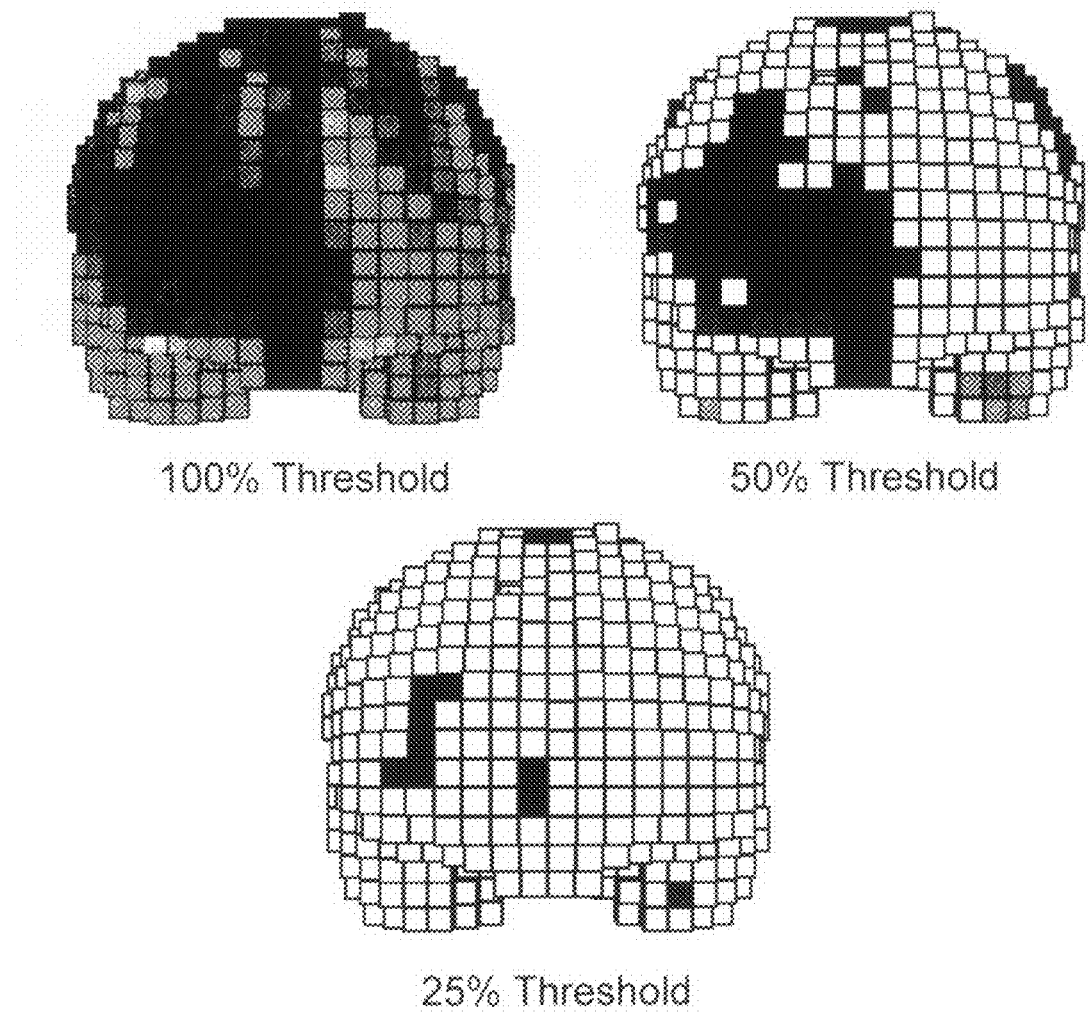
FIG. 5 depicts the variety of methods by which localized electrical activity can be graphically represented within a voxel.

FIG. 5G depicts the use of thresholds to limit the display of electrical activity to only those in a top percentage group, selected by the user. The top-left panel of FIG. 5G depicts 100% of the electrical activity, the top-right depicts the top 50% of activity, and the bottom-middle depicts only the top 25% of electrical activity within the solution space.

Group 3: Tools to Modify Graphically Displayed Results—FIG. 6

FIG. 6 depicts diagrams that demonstrate the various ways by which the graphical displayed results can be further modified.

Figure 6A:
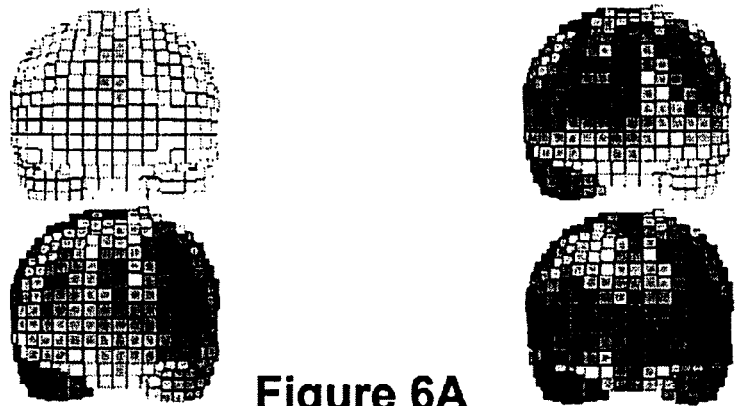
FIG. 6 depicts the variety of methods by which the graphical display result can be manipulated.

FIG. 6A depicts the utilization of multiple display windows. This is useful for examining several sources of data, or several aspects of a single recording at once. We achieve this by means of instantiating a number of new memory buffers and display windows corresponding to the number of windows desired to be displayed. The example depicted in this figure demonstrates the usage of multiple display windows to display the same data whose original EEGs have been filtered with multiple frequency parameters in near-real time; the top left image has been filtered between 1-3 Hz, top right 4-7 Hz, bottom left 8-12 Hz, bottom right 12-16 Hz. In addition to displaying the contents of multiple results in separate windows, they can be displayed in a single window, where each display result has a different color-key; this has also been reduced to practice but for practical reasons, cannot easily be depicted in the diagrams. These powerful features are very useful for such applications as sleep medicine and the monitoring of neurology patients.

Figure 6B:
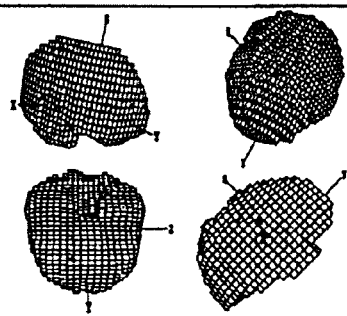

FIG. 6B depicts the tool for mouse-controlled free rotation. This is useful as the operator can in near-real time simultaneously observe the shifts in the electrical activity and perform mouse controlled free rotation manipulations of the display so as to observe all angles of the 3D cerebral cortex.

This gives the operator the power to see the cortex from any angle and not be restricted to fixed views such as front, back, bird's eye and side views (which is a drawback of tomography). We achieved this by generating a standard 3D rotation matrix from variables specifying the degrees of rotation around each of the 3 axes, X, Y, and Z, then using that matrix in successive transformations, in a manner well known to those skilled in the art.

Figure 6C:
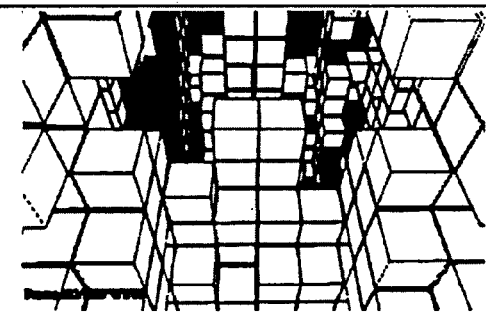

FIG. 6C depicts the tool for mouse-controlled brain panning. This is useful as it allows free movement outside and even inside the solution space to allow for the visualization of tiny areas within the cerebral cortex. We achieved this by generating a 3D translation vector from variables specifying the operator's 'camera' position in each of the 3 axes, X, Y, and Z, then using that vector in successive transformations, in a manner well known to those skilled in the art.

Figure 6D:
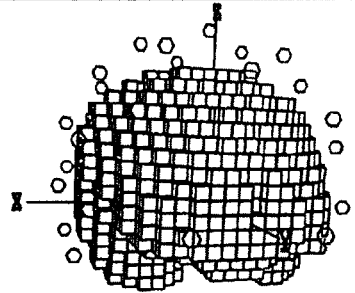
Figure 6E:
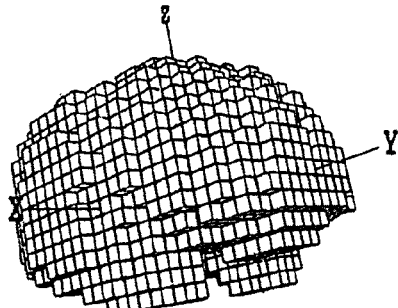

FIG. 6D depicts the tool for the display of electrode positions. This allows the operator to visualize, relative to the solution space, where the electrodes that collect the raw electrical signals have been placed. This is useful as it allows the operator to correlate the contribution of a particular electrode to the observed electrical activity. This was accomplished by drawing spheres at the 3D coordinates of the electrodes utilized by the present invention, transformed to the solution space coordinate system, dependant on which solution space is utilized.

FIG. 6E depicts the tool to mark axes. This is useful as when the cortex is imaged on a screen the operator can easily be disoriented and not know what part of the cortex they are looking at. This is especially true when the cortex is being rotated frequently by the mouse-controlled free rotation tool. We therefore have implemented a method to draw the X, Y, and Z axes of the cortex so as to aid the operator in knowing where up, down, left, right, front and back are. This was accomplished by drawing 3 lines, all originating from the center of the 3D solution space, and terminating at boundaries slightly larger than the dimensions of the solution space. At the line termini, text identifiers of each axis ("X", "Y", and "Z") are drawn.

Figure 6F:
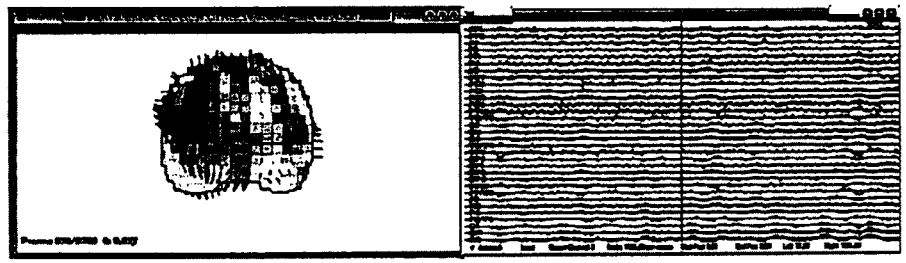

FIG. 6F depicts the tool to simultaneously display and navigate through EEG and 3D images. This is useful as people in the EEG field often have a considerable knowledge of cortical activity based on wave forms and spikes visible on EEG. We have observed in our own experience that there is a synergistic effect in making near-real time EEG and near-real time 3D cortical imaging visible to the operator simultaneously. We have implemented this in a manner which time locks the EEG signal display and the corresponding 3D images so as to allow the operator to correlate the two, and this feature is available in near-real time. This has been reduced to practice as part of the invention's custom software, as shown in this figure.

FIG. 6G depicts the tool for the near-real time display of the name, location, and current density of a voxel. This is accomplished by drawing the number, numerical value of the current density, location in the solution space, and neuroanatomical regions of a selected voxel into a window for the current instance in time.

FIG. 6H depicts the tool for the alphanumeric display of a predetermined list of voxels in near-real time. The voxel number, hemisphere (side), the associated Brodmann area (a neuroanatomical classification system based on human brain histology developed by Korbinian Brodmann in 1909), major anatomical region, minor anatomical region, the magnitude of the electrical activity (current density) at the current instant in time, and the x-component, the y-component, and the z-component of electrical activity vector at the current instant in time are all displayed as alphanumeric text in a window. This is accomplished by drawing the values for these aforementioned fields that already exist in memory from preceding calculations or stored tables, as text in the window.

Methods of Application of the Present Invention—FIGS. 7-15

FIGS. 7-15 depict flowcharts that describe the steps involved in the utilization of the present invention and its intended applications. The solid boxes represent required steps, while the dashed boxes represent optional steps. The arrows represent sequential orders of execution beginning with the steps connected to the tail ends of the arrows, then ending with the heads of the arrows. Hollow diamond shapes with solid borders represent decision steps, and the filled octagons represent termination steps, where operation of the present invention ceases. Smaller symbols that appear inside steps are represented as follows; solid triangle for a step requiring the human operator to interpret a result or alert; solid square for a step requiring the human operator to select a parameter or purpose; and a solid diamond for a step requiring the human operator to setup an apparatus.

A Preferred Embodiment of the Present Invention and its Particular Applications—FIG. 7

FIG. 7 depicts a master flowchart for the 8 applications of the present invention along with steps that are required for all 8, and optional steps that are application specific pertaining to analysis, and setup of the application.

Figure 7A:
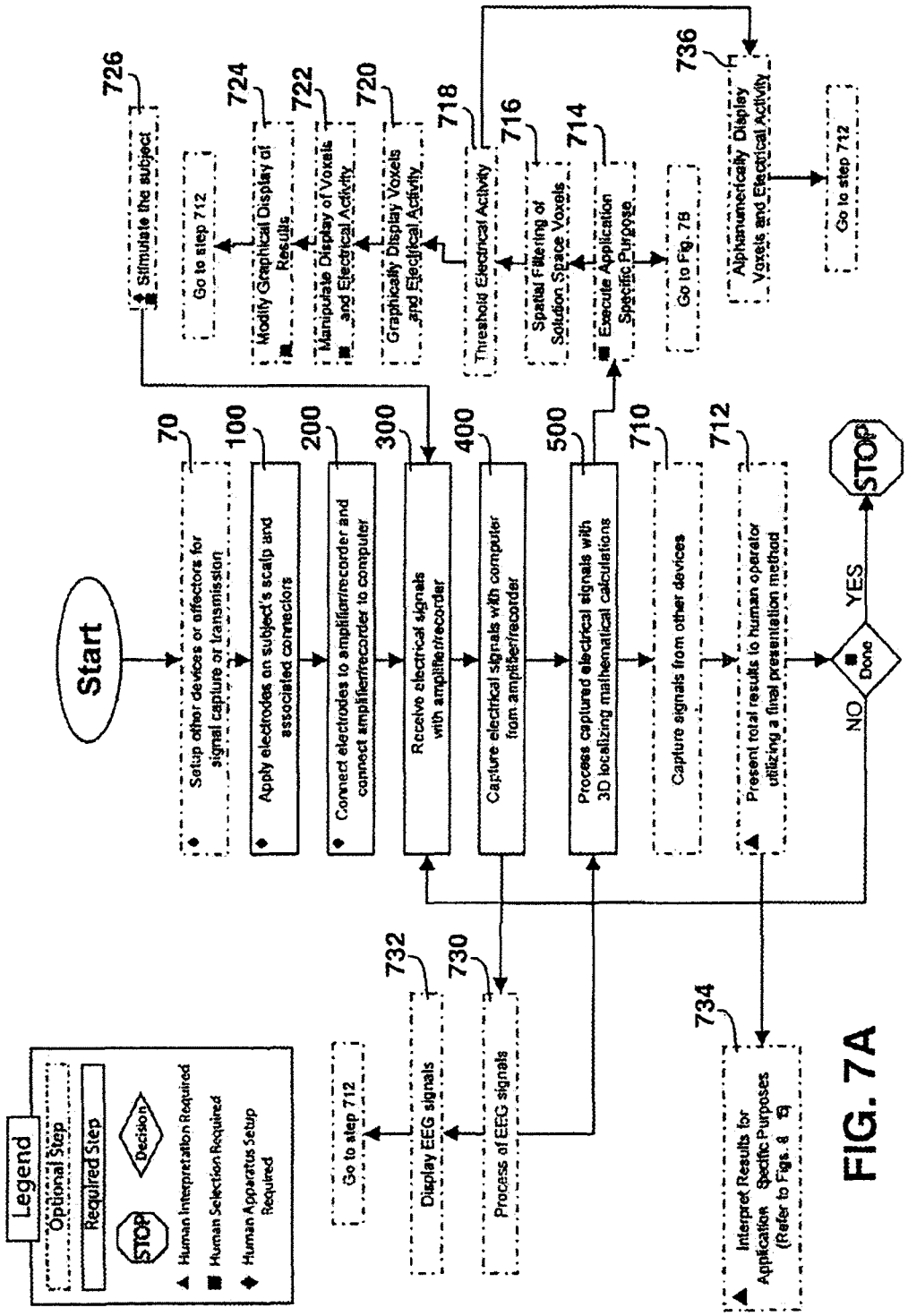
FIG. 7 depicts a master flowchart of the present invention outlining the possible methods involved in the capture, localization, display and analysis of electrical signals from the cerebral cortex, and its applications. The applications of the present invention include diagnosing, monitoring, treating, researching, lie detecting, educating the brain, and entertaining.

FIG. 7A describes an extended scheme by which the present invention operates in a preferred embodiment, whereas FIG. 1 depicted the most basic embodiment. Steps 100-500 in FIG. 7A are identical to those in FIG. 1, hence do not need to be described again. However, following step 500, the present invention may optionally be involved in executing a particular application (listed in FIG. 7B, and further described in FIGS. 8-15), chosen by the human operator, as depicted by step 714.

The execution of a particular application may involve the further spatial filtering of voxels, by which only those voxels that are deemed by the application to be relevant or of interest are included in subsequent calculations, as depicted by step 716. Step 718 depicts the optional step where only voxels exceeding or falling within a certain threshold of electrical activity would be included in subsequent calculations; for example, only those voxels that are in the bottom 50% of electrical activities at the present time would be included in further steps. Step 720-724 refers to the optional display and manipulations of the voxels and localized electrical activity, as previously described in FIGS. 4-6. At this point, the displayed voxels and localized electrical activity may optionally then be incorporated into the final presentation method, described further below and depicted in step 712. Alternatively, instead of graphically displaying the localized electrical activity, as in steps 720-724, the localized electrical activity may be displayed as alphanumeric text, as demonstrated in FIG. 6H and depicted in step 736, followed by the optional incorporation into the final presentation method, depicted by step 712.

Step 710 depicts the optional acquisition of signals in near-real time from other devices, such as those that capture video, audio, physiological parameters, or information from remote locations (as in the case of telemedicine), which could then further contribute to the function and operation of the invention.

Step 70 depicts the setting up of the other devices or effectors involved in the acquisition of additional signals, manipulating the environment, or functioning as transmitters to remote locations. This is further elaborated upon in FIG. 7C.

Step 712 entails a final presentation method to present results to the human operator of the invention, which generally may be any one or combination of the items below:
  i) a single screen display with one window,
  ii) a single screen display with multiple windows,
  iii) a multiple screen display with single windows,
  iv) a multiple screen display with multiple windows,
  v) an audio speaker.

The selection of the type of final presentation method will depend on the particular application of the present invention.

Following step 712, the human operator may interpret the results presented using the final presentation method and then act accordingly, depending on the intended application for the present invention, as depicted in step 734.

Step 730 follows step 400, the capturing of electrical signals (EEG signals, since they originated from the cerebral cortex) from the amplifier/recorder, and it depicts the optional further processing of the EEG signals, that extends beyond the filtering described in step 400; this may include examining the signals for certain features or thresholding activity originating from within any or all electrodes.

Step 732 follows step 730, in that the EEG signals may then be displayed on a screen, and optionally further incorporated into the final presentation method in step 712. This has been reduced to practice as part of the invention's custom software, as shown in the right panel of FIG. 6F. This was accomplished by drawing onto the display each electrode name on the screen in a vertical list, and for each electrode, drawing lines connecting each data point (with each point representing the electrical potential read from the electrode and captured with the computer from the amplifier/recorder at that time in the Y axis and the time of capture in the X axis), preceding the present time.

Stimulation of the subject, depicted in step 726, may also be an optional step during the operation of the present invention (depicted as leading into step 300, the start of the near-real time loop of operation) as it may be a relevant requirement of the chosen application of the present invention. This stimulation may be performed in several ways:
  a) auditory stimulation, such as the playing of sounds or audio recordings with a speaker, or live in the subject's environment,
  b) visual stimulation, such as the presentation of images,
  c) tactual stimulation, such as light touch, or mechanical stimulation,
  d) olfactory stimulation, such as the presentation of smell,
  e) internal chemoreceptor stimulation, such as the alteration of blood pH,
  f) thermal stimulation, such as the presentation of a cold stimulus,
  g) nociceptive stimulation, such as the presentation of a painful mechanical stimulus,
  h) proprioceptive stimulation, such as the disruption of self-awareness,
  i) equilibrioceptive/vestibular system stimulation, such as the disruption of the inner-ear fluid to upset balance, and
  j) stimulations which evoke a specific emotion using a complex sensory stimulus and cognitive stimulation including the presentation of an idea or words or presentation of any cognitive stimulus such as one that evokes a mental change such as the recall of a memory.

FIG. 7B lists the eight particular applications of the present invention, and serves as an index for which figure further explains each application. Each application originates from FIG. 7A, step 714, which calls for the execution of a particular application, decided by a human operator. The applications and their associated figures are as follows:
  a) Researching—FIG. 8,
  b) Diagnosing—FIG. 9,
  c) Monitoring—FIG. 10,
  d) Treating—FIG. 11,
  e) Lie Detecting—FIG. 12,
  f) Educating the Brain—FIG. 13,
  g) Entertaining—FIG. 14, and
  h) Effecting an Industrial Process—FIG. 15.

Figure 7C:
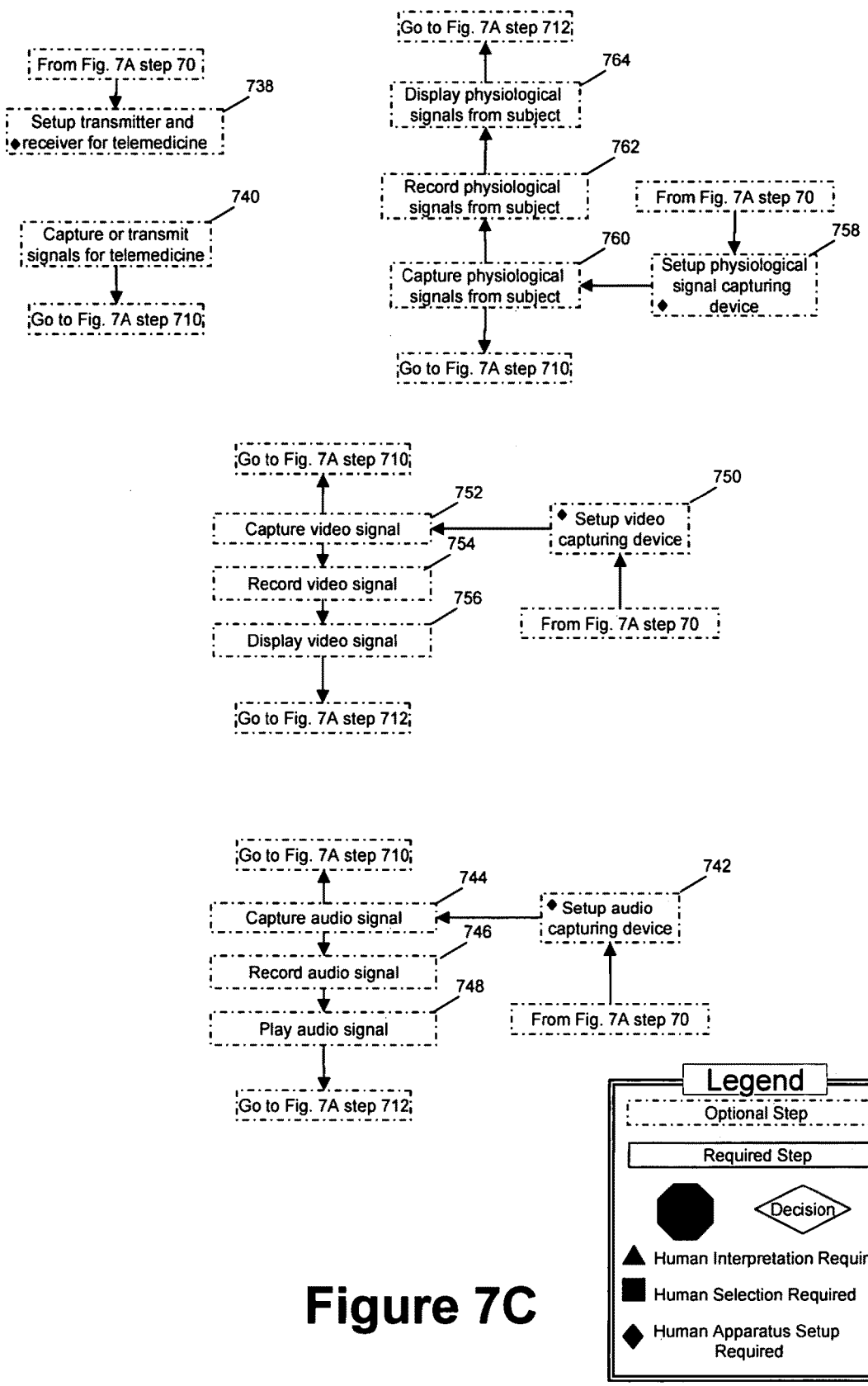

FIG. 7C depicts the setup and utilization of the other devices or effectors mentioned in FIG. 7A, steps 70 and 710. Some particular applications may require or may benefit from additional information that supplements the subject's localized electrical activity. For example, in the case of sleep medicine it is relevant to collect physiological signals from a subject, such as those from an oxygen monitor, to determine the breathing status of the subject. Some particular applications may require transmitters and receivers to send and receive a subject's localized electrical activity between remote locations, such as in the case of telemedicine, where the human operator that would interpret a subject's condition may be located hundreds of kilometers away.

Step 738 depicts the setup of a transmitter and receiver for the purpose of telemedicine. The transmitter could be anything capable of sending a signal with sufficient bandwidth to capture the near-real time localized electrical activity data. This could be performed over a private network, the internet, or through wireless transmission of electromagnetic radiation with wavelengths similar to those use by radio or television broadcasts. The transmitter would be located at the site where the subject is located and connected to the present invention. The receiver would be at a remote location and would use the same medium of communication that the transmitter would use, and it would be connected to an alternate 'remote site' embodiment of the present invention where the receiver would generate the electrical activity signals as opposed to a computer transforming electrical signals captured from an EEG amplifier/recorder. Step 740 depicts the operation of the aforementioned transmitters and receivers. Data would be transmitted at the subject site prior to FIG. 7A step 710, and the data would be received at the remote site before FIG. 7A step 710 in the 'remote site' embodiment of the present invention.

Steps 742-748 depict the setup, capturing, recording and playing of an audio signal. The audio signal capturing device, such as a microphone connected to a soundcard in a computer, would be connected in step 742 following FIG. 7A step 70. During the operation of the present invention, audio signals may then be captured for use by the present invention in FIG. 7A step 710 as depicted in step 744, recorded as in step 746, or played as in step 748. Audio signals may be recorded to random access memory, on an external media such as a CD, DVD or cassette, or onto a hard drive. Playing of the audio signal could be integrated with the final presentation method in FIG. 7A step 712, or accomplished using a standalone loud-speaker or equivalent.

Steps 750-756 depict the setup, capturing, recording and playing of a video signal. The video signal capturing device, such as a digital camera or camcorder connected to a video card in a computer, would be connected in step 750 following FIG. 7A step 70. During the operation of the present invention, video signals may then be captured for use by the present invention in FIG. 7A step 710 as depicted in step 752, recorded as in step 754, or displayed as in step 756. Video signals may be recorded to random access memory, on an external media such as a CD, DVD or cassette, or onto a hard drive. Displaying of the video signal could be integrated with the final presentation method in FIG. 7A step 712, or accomplished using a standalone monitor or equivalent.

Steps 758-764 depict the setup, capturing, recording and playing of physiological signals. Examples of physiological signal capturing devices include:
  a) electrooculogram,
  b) electromyogram,
  c) electrocardiogram,
  d) strain gauges,
  e) piezoelectric bells,
  f) inductive plethysmography,
  g) impedance gauge,
  h) pneumograph,
  i) endoesophageal pressure monitor,
  j) air flow thermistor,
  k) pneumotachograph,
  l) oxygenator,
  m) body position monitor,
  n) vibration monitor,
  o) end tidal $CO_2$ monitor,
  p) transcutaneous $CO_2$ monitor,
  q) esophageal PH monitor, penile
  r) tumescence monitor,
  s) galvanometer,
  t) sphygmomanometer, and
  u) heart rate monitor.

Any one of these devices, or any combination of them may be connected to the present invention in step 758 following FIG. 7A step 70. During the operation of the present invention, physiological signals may then be captured for use by the present invention in FIG. 7A step 710 as depicted in step 760, recorded as in step 762, or displayed as in step 764. Physiological signals may be recorded to random access memory, on an external media such as a CD, DVD or cassette, or onto a hard drive. Displaying of the physiological signals could be integrated with the final presentation method in FIG. 7A step 712, or accomplished using a standalone monitor or equivalent.

Figure 8:
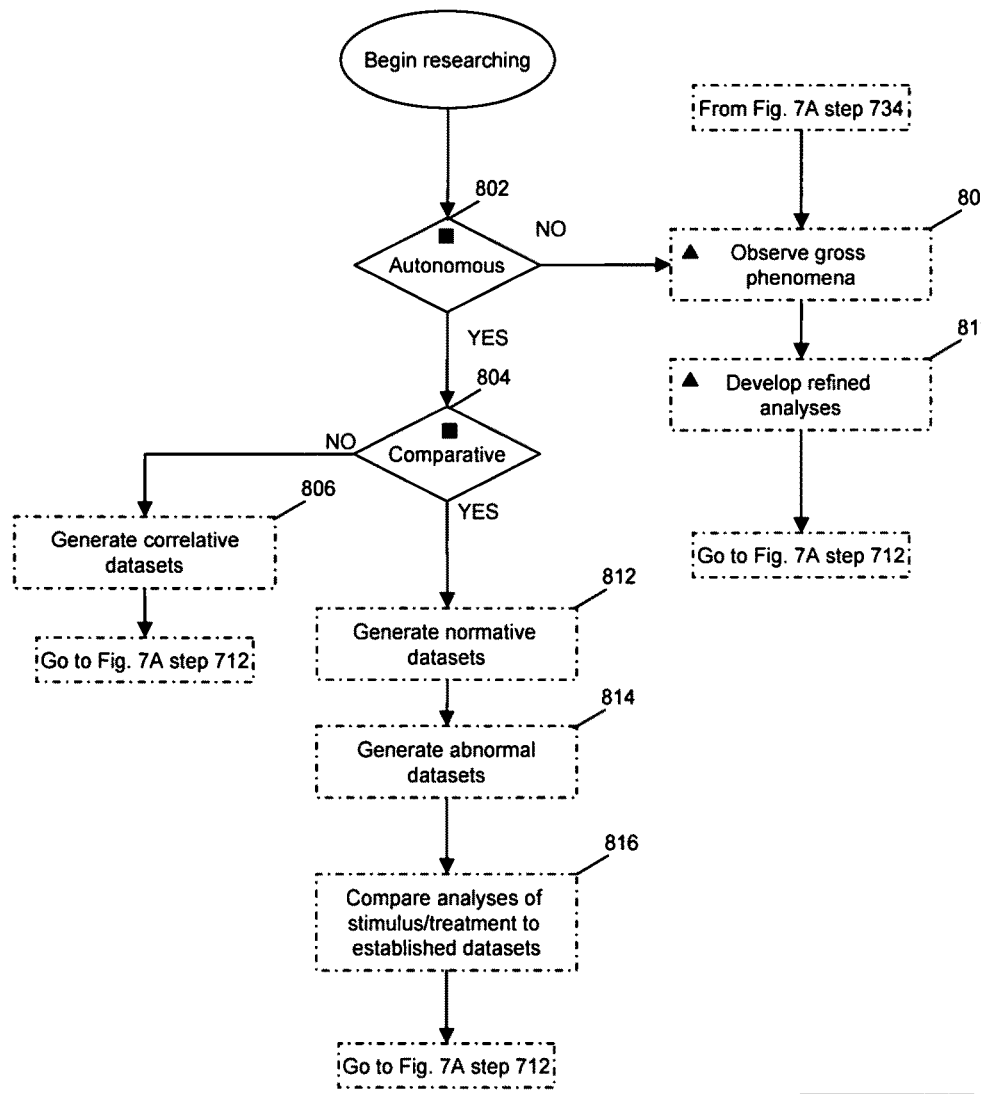
FIG. 8 depicts a flowchart which is an extension of FIG. 7 whereby a human operator has decided to utilize the present invention for the purpose of researching.

Methods of Researching Utilizing the Present Invention—FIG. 8

FIG. 8 depicts how the present invention may be utilized to discover a wide variety of information and insight on the involvement of the cerebral cortex by its localized electrical activity through conducting research in near-real time. This research will generate quantitative datasets on normal and abnormal conditions, disorders, and states. Examples of these datasets include:
  i) brain disorders,
  ii) changes in the conditions of subjects with brain disorders,
  iii) normal brain processes,
  iv) characterization of the synergy between functional elements of the brain (i.e. areas of the brain that work together to perform a function),
  v) cortical targets for treating diseases,
  vi) lying,
  vii) telling the truth,
  viii) thoughts and ideas,
  ix) feelings and emotions,
  x) sensations,
  xi) beliefs,
  xii) predispositions,
  xiii) planning, and
  xiv) psychological states of mind.

In order to perform many of the particular applications of the present invention listed in FIG. 7B, including diagnosing, monitoring (especially for an improvement or deterioration), treating, lie detecting, educating the brain, entertaining and effecting an industrial purpose, it will be necessary to first conduct research on subjects to establish parameters such as:
  i) what is normal, to provide a basis of comparison towards,
  ii) what is abnormal (i.e. the signature or pattern of a particular condition, disorder or state),
  iii) thresholds, that when exceeded or have fallen below, signify something important, and
  iv) correlations between two or more variables, so that if one variable changes or can be changed, the response of the other, or others, can reliable be predicted.

There are two ways to establish these parameters, as mentioned by the decision step 802; autonomously and non-autonomously. An autonomous way of establishing parameters involves the processing of the localized electrical activity information by algorithms, without human involvement, whereas the non-autonomous establishment of these parameters initially involves a human operator observing gross phenomena, which is step 808.

The observation of gross phenomena, depicted by step 808, means that there are changes that are noticeably visible to the operator of the present invention. One important type of observable gross phenomena is a correlation such as when the operator can see a noticeable change in a subject's near-real time localized electrical activity and other cues such as gross deflections on the simultaneous near-real time EEG signals or physiological signals. These changes would be observed using the final presentation method and initial interpretation mentioned in FIG. 7A step 734. However, there may other cues involved that are not related to the collection of signals, such as gross facial expressions as well as audible utterances, and gestures. After forming a judgment as to the occurrence of a correlation, the operator may use the present invention to deconstruct the associated 3D signal. For example, if one sees an interesting feature on EEG and associated localized electrical vectors that point away from that electrode's position adjacent to the solution space, then one can play back the display in slow-motion and perform simultaneous viewing so as to isolate precisely which vectors are most responsible for the observation of gross phenomena. This may require the utilization of a number of the tools or procedures described in this document as well as any sort of stimulus previously mentioned.

If the parameters mentioned in section [00099] are to be established autonomously, then the decision in step 804 must be made; is the parameter going to involve a comparison, or will it depend on a correlation? If the answer is yes, then the generation of normative datasets and abnormal datasets must occur (steps 812 and 814). If the answer is no, then correlative datasets must be generated (step 806).

Calculating statistical norms requires normal data. Step 812 depicts the generation of normative data for the purpose of establishing a statistical norm. This entails the near-real time collection of localized electrical activity from a number of subjects that are healthy and are not afflicted by the condition, state or disorder that the particular research application is attempting to identify. It is possible to accomplish this in a way such that as the present invention is operating, the normative dataset would continually be added to, if the data is being stored in near-real time, either in the form of captured electrical signals, localized electrical activity, or processed localized electrical activity. In addition this same method can be utilized to generate a normative dataset for a patient's own healthy state.

Generating an abnormal dataset, as mentioned in step 814, requires a similar procedure with the exception that subjects are now required to be afflicted or expressing the condition, state or disorder that the research application is attempting to identify.

It is possible to generate both normative and abnormal datasets in near-real time on the basis of the following items:
  i) *Average or standard deviation of the current density for each voxel over time,
  ii) *Average or standard deviation of the x, y, and z components of the localized electrical activity vectors for each voxel over time,
  iii) *Average or standard deviation of the localized electrical activity vector rotation over time,
  iv) *Average rate of change of items i-iii above (i.e. velocity),
  v) Median or mode of the current density for each voxel over time,
  vi) Median or mode of the x, y, and z components of the localized electrical activity vectors for each voxel over time,
  vii) Median or mode of the velocity of electrical activity vector rotation over time,
  viii) Average rate of change of items v-vii above (i.e. velocity),
  ix) Average acceleration (i.e. rate of change of velocity) of items i-vi above, and
  x) Average counts for a specific current density pattern in time such as the number of occurrences or frequency of spikes (a sudden increase in current density) over time.

Note: on items marked with an asterisk (*), the present invention has reduced to practice via the custom software.

The near-real time averaging of values and calculation of standard deviations was accomplished by continuously adding the values in question (i.e. current densities, electrical activity vectors, or electrical activity directions) (v) into an memory buffer over time (V) and then dividing by the number of instances in time, or frames that have elapsed (n). In addition, the standard deviation (s) at any given moment can be obtained by the following well-known formula: $s=\sqrt{(\Sigma(v-V)^2/(n-1))}$. Alternatively, averaging in near-real time over a period of time for any sort of item mentioned can be accomplished by calculating a weighted average between the previously calculated average and the current value. For example, if the invention has been operating for 1000 instances in time, or frames, to calculate the average at frame #1001, one would add the value at the current time, frame #1001, divided by 1001, to the previous average calculated over the past 1000 frames multiplied by 1000/1001.

Calculating the change or instantaneous velocity of a vector component, angle, or current density was accomplished by taking the difference between the value at the current frame and the value at the previous frame.

Calculating the rotation of the electrical activity vectors was accomplished by normalizing the vector by its magnitude, as previous described in FIG. 5F.

Once the datasets have been generated, comparisons can take place, as denoted by step 816, to ask such questions as:
  i) Are these abnormal datasets significantly different from what is known to be normal?
  ii) Is this subject with the condition, state or disorder that the research application is attempting to characterize the same as all the other abnormal datasets?
  iii) Is this subject really normal?

To answer the above questions, statistical tests between the two datasets have to be performed. It is possible to use tests such as t-tests and its derivatives, Poisson tests, $X^2$ tests, analysis of variance (ANOVA), topographical analysis of variance (TANOVA), multiple analysis of variance (MANOVA), general linear model (GLM) tests, statistical parametric mapping (SPM) and statistical non-parametric mapping to do this. The results of these tests could then be presented using the final presentation method, FIG. 7A step 712. Both t-tests and Poisson tests have been reduced to practice by the present invention via the custom software. This was accomplished utilizing techniques known to those skilled in the art.

To generate a correlative dataset, a similar approach to the generation of a normative or abnormal dataset can be undertaken, only that instead of establishing a comparison, a correlation between two or parameters would be generated instead, as mentioned in step 806. Based on the correlative data generated, thresholds can then be defined. For example, in section [00026] it was mentioned that alcohol intoxication exhibited increased theta activity; if one were to measure a subject whose level of intoxication was steadily increased through the consumption of a certain fermented hops and barley containing beverage and the subject's captured electrical signals were filtered for the theta range of frequencies then processed into localized electrical activity, one could plot a correlation between frontal lobe theta band localized electrical activity and level of intoxication in near-real time. One could also repeat this in a number of subjects to build a correlative index with a higher statistical power. The results of these correlative studies could then be presented using the final presentation method, FIG. 7A step 712. In the context of the above example, if one were to then finally examine and interpret the correlative data, one could determine a quantitative threshold based on the theta band localized electrical activity defining at what level of activity a subject would be considered to be legally intoxicated.

An additional important step in these aforementioned methods of research is the utilization of a stimulus applied to a subject to test for a response. This is encompassed by FIG. 7A step 726. The present invention has been designed to perform this type of research. Research into the mechanism of action of drugs and into the discovery of characteristics of lying may be performed using this method.

Figure 9:
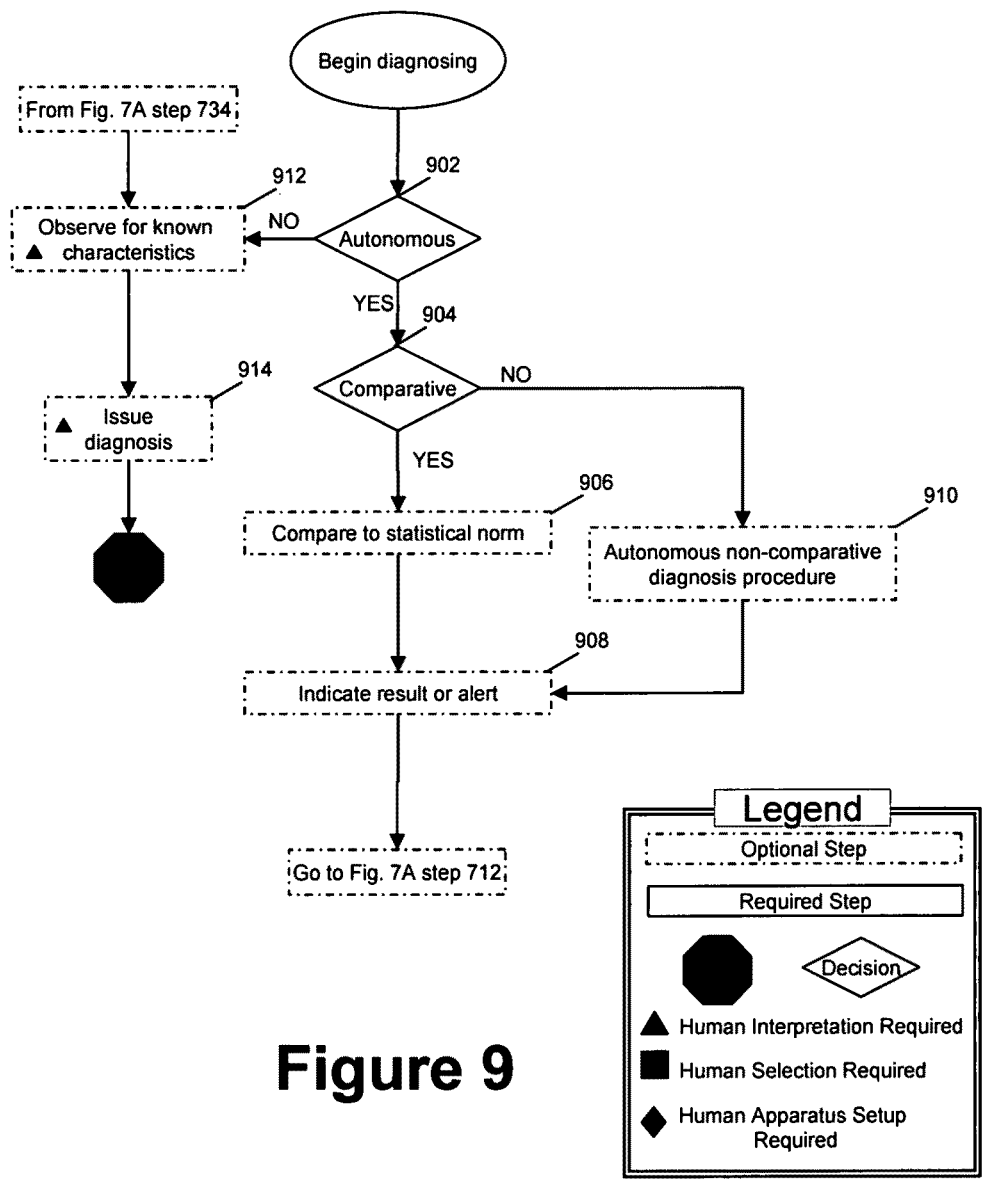
FIG. 9 depicts a flowchart which is an extension of FIG. 7 whereby a human operator has decided to utilize the present invention for the purpose of diagnosing.

Methods of Diagnosing Utilizing the Present Invention—FIG. 9

FIG. 9 depicts how the present invention can be utilized to diagnose the wide variety of brain disorders mentioned in section [00026]. The research application described in FIG. 8 is very important in establishing the diagnostic parameters, patterns and datasets required for the use of this invention in diagnosis, hence many of the methods utilized by this application are similar if not identical to those in the researching application.

The present invention has three principle methods to diagnosing brain disorders. Two are autonomous and one is not, with the differences between the two approaches described previously in FIG. 8. Step 902 is where the decision to use an autonomous method is made, and the particular choice depends on the suspected brain disorder or provisional diagnosis made by a clinician. This decision may not require human choice as it may be predetermined depending on the disorder.

The non-autonomous method is based on observation for known characteristics, as depicted in step 912. Observation in this case means that the human operator is utilizing the final presentation method and interpretations thereof from FIG. 7A step 734, with all necessary potential signals (FIG. 7C), and tools for manipulating electrical activity (FIGS. 4-6) at the operator's disposal to make a diagnosis based on the operator's own experience in utilizing the present invention and interpreting for the particular brain disorder or brain disorders to be diagnosed in the patient. At this point the operator can then issue a diagnosis, as depicted in step 914, followed by the termination of the operation of the present invention as the procedure has been completed.

The autonomous methods are further divided into comparative and non-comparative methods at the decision made in step 904. This decision may not require human choice as it may be predetermined depending on the disorder.

Step 906 represents the autonomous comparative method where the patient's localized electrical activity is processed as mentioned in FIG. 8 and compared to either the patient's own normal dataset, or a normative dataset that is a statistical norm for healthy individuals not suffering from the patient's suspected condition. The comparison would be performed utilizing a number of statistical tests, described in FIG. 8.

Step 910 represents the autonomous non-comparative method where the patient's localized electrical activity is processed as mentioned in FIG. 8 and relevant activity assessed to see if it is crossing over or under a threshold derived from either the patient's own correlative dataset, or a correlative dataset from a number of patients.

Upon the completion of either autonomous test, a result or an alert would be indicated in step 908, which could be interpreted by the operator either before or after integration into the final presentation method (FIG. 7A step 712).

Figure 10:
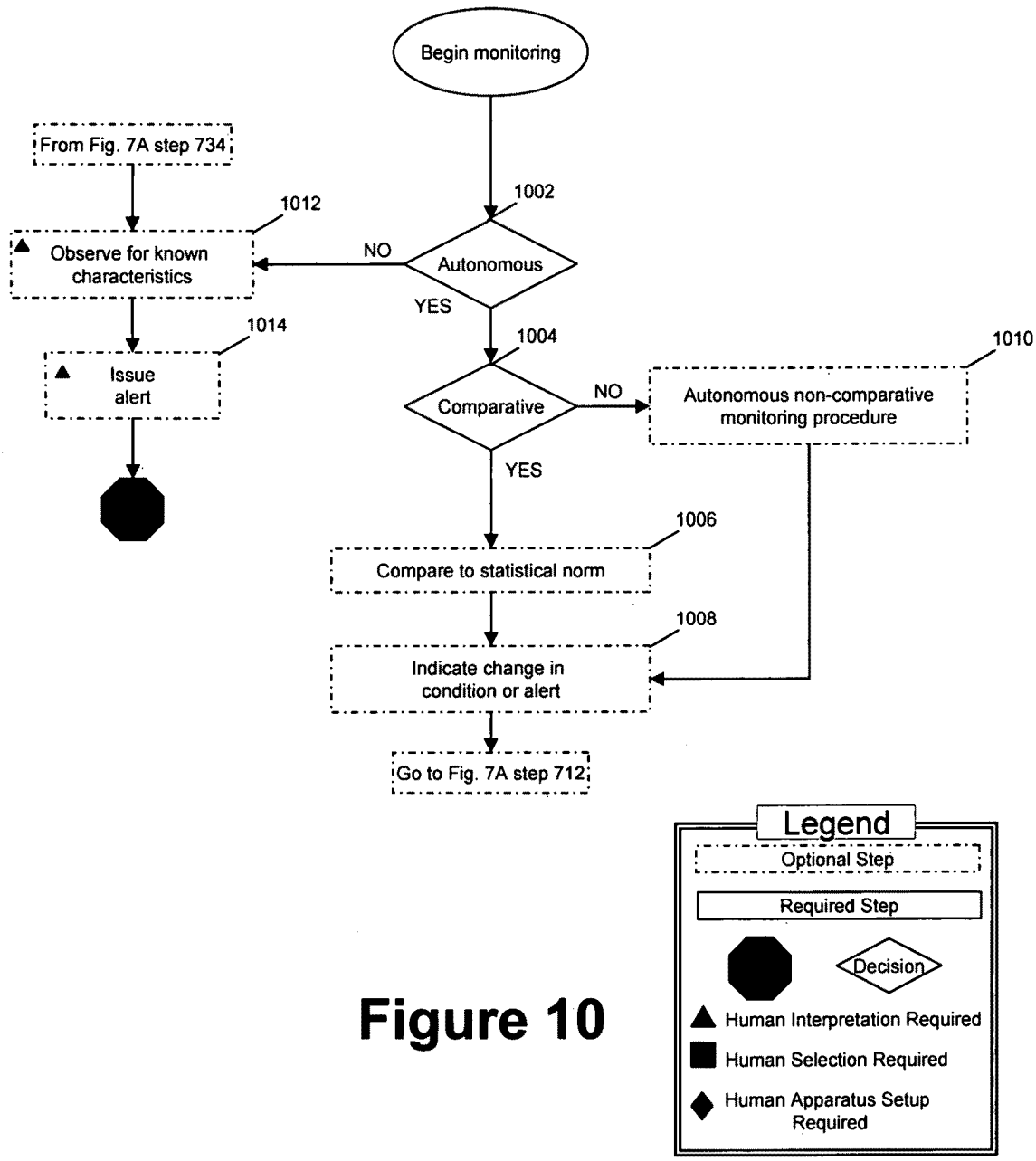
FIG. 10 depicts a flowchart which is an extension of FIG. 7 whereby a human operator has decided to utilize the present invention for the purpose of monitoring.

Methods of Monitoring Utilizing the Present Invention—FIG. 10

FIG. 10 depicts how the present invention can be utilized to monitor the wide variety of monitorable conditions that consists of the brain disorders and conditions mentioned in sections [00026-00027]. Monitoring provides a flow of information in near-real time either locally to an observer that is in the presence of the patient or to a remote observer, by means of telemedicine techniques. Monitoring can be achieved using of audio, visual, or mechanical alarms as opposed to display monitors, and when alarms are involved, a visual display monitor may not be required.

Many of the methods utilized by this application are similar if not identical to those in the researching and diagnosing applications.

Step 1002 is describes the situation wherein a decision to use an autonomous method is made, and the particular choice depends on the patient's monitorable condition. This decision may not require human choice as it may be predetermined depending on the monitorable condition.

The non-autonomous method is based on observation for known characteristics, as depicted in step 1012. The operator performs this observation utilizing the tools and methods of the invention in addition to drawing upon the experience of the operator in recognizing changes in the monitorable condition. When a change is observed, the operator can then issue an alert, as depicted in step 1014, followed by the termination of the operation of the present invention as the procedure has been completed.

The autonomous methods are further divided into comparative and non-comparative methods at the decision made in step 1004. This decision may not require human choice as it may be predetermined depending on the monitorable condition.

Step 1006 represents the autonomous comparative method where the patient's localized electrical activity is processed as mentioned in FIG. 8 and compared to either the patient's own normal dataset, or a normative dataset that is a statistical norm for healthy individuals that are not exhibiting the patient's monitorable condition. The comparison would be performed utilizing a number of statistical tests, described in FIG. 8.

Step 1010 represents the autonomous non-comparative method where the patient's localized electrical activity is processed as mentioned in FIG. 8 and relevant activity assessed to see if it is crossing over or under a threshold derived from either the patient's own correlative dataset, or a correlative dataset from a number of patients.

Upon the completion of the autonomous test, a result or an alert indicating a chance in condition would be indicated in step 1008, which could be interpreted by the operator either before or after integration into the final presentation method (FIG. 7A step 712), or interpreted by the patient if a portable embodiment of the invention is utilized.

Figure 11:
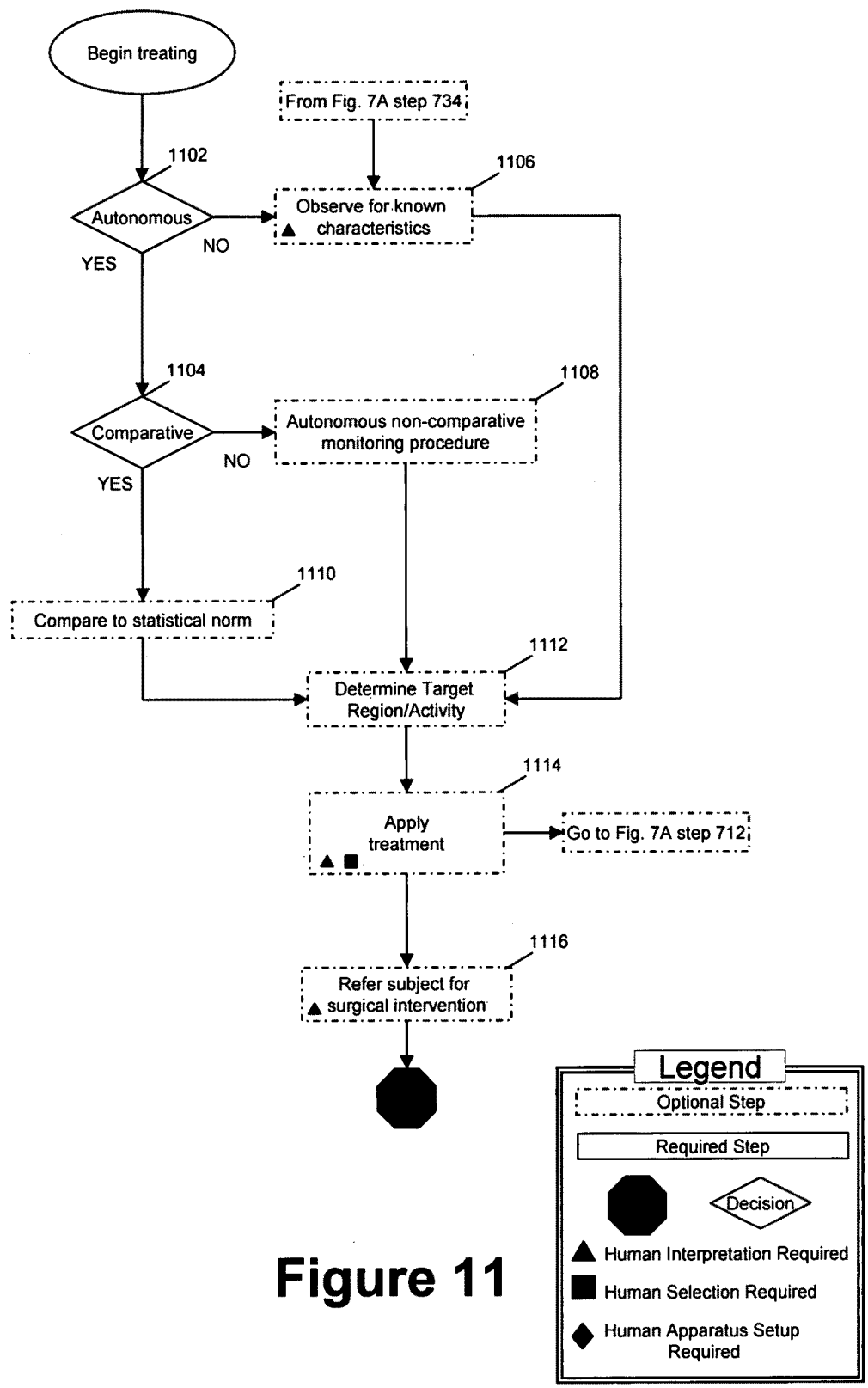
FIG. 11 depicts a flowchart which is an extension of FIG. 7 whereby a human operator has decided to utilize the present invention for the purpose of treating.

Methods of Treating Utilizing the Present Invention—FIG. 11

FIG. 11 depicts how the present invention can be utilized to treat the wide variety of treatable conditions that consists of the brain disorders and treatable conditions mentioned in sections [00026-00028].

In general, the role of the present invention in the realm of treatment is to serve as a guidance system to help target a particular treatment. This would be accomplished by using the present invention to isolate a target region or a target electrical activity pattern which is characteristic of a treatable condition. Subsequently a corrective action is taken using any of a number of treatment modalities, described below.

Many of the methods utilized by this application are similar if not identical to those in the researching, diagnosing, and monitoring applications.

Step 1102 is where decision to use an autonomous method is made, and the particular choice depends on the patient's treatable condition. This decision may not require human choice as it may be predetermined depending on the treatable condition.

The non-autonomous method is based on observation for known characteristics, as depicted in step 1106. The operator performs this observation utilizing the tools and methods of the invention in addition to drawing upon the experience of the operator in recognizing regions or activities as potential targets in the treatable condition, as shown in step 1112.

The autonomous methods are further divided into comparative and non-comparative methods at the decision made in step 1104. This decision may not require human choice as it may be predetermined depending on the treatable condition.

Step 1110 represents the autonomous comparative method where the patient's localized electrical activity is processed as mentioned in FIG. 8 and compared to either the patient's own normal dataset, or a normative dataset that is a statistical norm for healthy individuals that are not exhibiting the patient's treatable condition. The comparison would be performed utilizing a number of statistical tests, described in FIG. 8.

Step 1108 represents the autonomous non-comparative method where the patient's localized electrical activity is processed as mentioned in FIG. 8 and relevant activity assessed to see if it is crossing over or under a threshold derived from either the patient's own correlative dataset, or a correlative dataset from a number of patients.

Upon the completion of the autonomous test, regions or activities would be identified as potential targets for the treatable condition, as shown in step 1112.

When a target has been identified, the operator can then proceed with administering a treatment, as depicted by step 1114, such as a non-invasive treatment with a transcranial magnetic stimulation (TMS) device, or an entrainment device. Entrainment devices are used to attempt to modify the electrical activity in the patient's brain, generally to bring about a beneficial effect. Such devices may stimulate the patient visually, acoustically or via another sensory modality. TMS devices utilize magnetic fields to modify the patient's brain electrical activity. At this point the results of the treatment may be observed using the final presentation method (FIG. 7A step 712) for effectiveness.

In addition, the operator may want to refer the patient for a surgical intervention, such as the implantation of a stimulatory or inhibitory device to invasively treat the target. At this point the operation of the present invention will terminate as the procedure has been completed.

Figure 12:
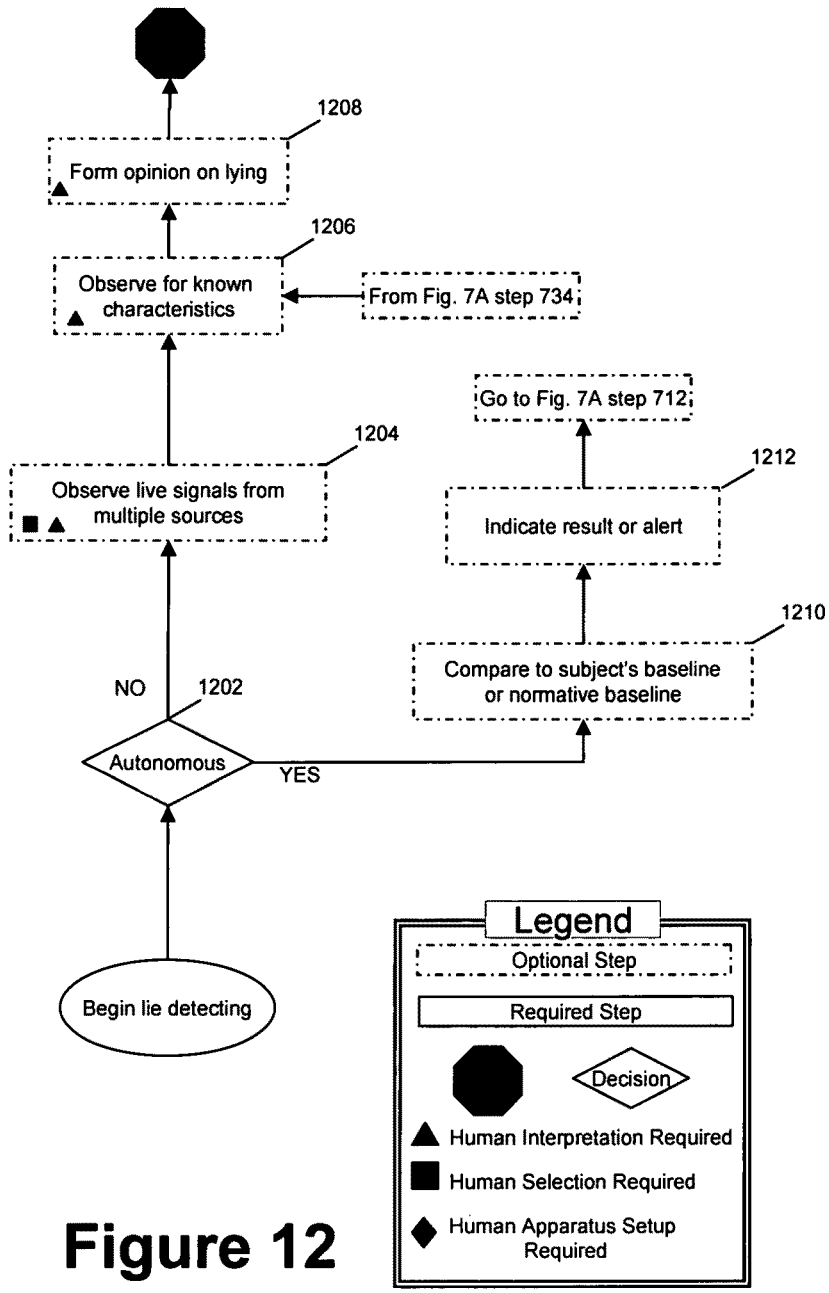
FIG. 12 depicts a flowchart which is an extension of FIG. 7 whereby a human operator has decided to utilize the present invention for the purpose of lie detecting.

Methods of Lie Detecting Utilizing the Present Invention—FIG. 12

FIG. 12 depicts how the present invention can be utilized to detect whether a subject is lying or telling the truth. In order to develop this application, signature patterns for localized near-real time electrical activity indicative of lying and truthfulness may be identified through research trials utilizing the present invention and methods previously described in FIG. 8.

To elaborate, the trials may involve generating datasets from subjects who are instructed to lie or instructed to tell the truth and who comply with this request while connected to the present invention. These datasets of truths and lies may later be used when testing future subjects for lying and may serve as a basis for comparison.

The first specific step in the lie detecting application is the decision step 1202 asking whether to use an autonomous method. The answer depends on the results of the research trial into the most accurate determining test for truthfulness. If the trial indicates that the non-autonomous method is ideal (akin to how polygraphs are still completely human-interpreted), then steps 1204-1208 will commence afterwards; otherwise, steps 1210-1212 will.

The subject would then be stimulated, as previously described in FIG. 7 step 726, where in this case, the stimulus could be in the form of a question that would elicit a response from the subject, which may or may not be a truthful one. It may also involve other forms of stimulation such as showing someone an object. In some instances no question is asked and the subject's electrical activity is studied for known indicators of lying.

Step 1204 is an optional step that involves the observation of a single or any combination of additional near-real time signals from other signal acquisition devices such as those previously described in FIG. 7C. Each of these signals may have characteristic markers for lying including previously known physiological markers for lying, video markers for lying (such as facial expressions and gestures), or near-real time audio markers of lying.

Step 1206 involves the observation for known characteristics utilizing interpretation of the final presentation method from FIG. 7A step 734. The human operator may utilize any single tool or combination of tools for manipulating electrical activity (FIGS. 4-6) to assist in the isolation of the localized activity specific to lying and truthfulness.

Based on the observations from step 1206, the human operator would then form an opinion on lying. At this point the application would be complete, and the operation of the present invention terminated.

If the autonomous method of determining truthfulness was demonstrated to be ideal, then step 1210 would execute, the subject's localized electrical activity would be compared, using the previously described statistical tests, to the subject's own baseline (normal truthful state), or a baseline generated from a number of healthy truthful subjects in an identical way that the normative dataset would be generated from FIG. 8.

At this point, a result or alert on the subject's truthfulness would be indicated by the statistical test utilized, and incorporated into the final presentation method in FIG. 7A step 712.

Figure 13:
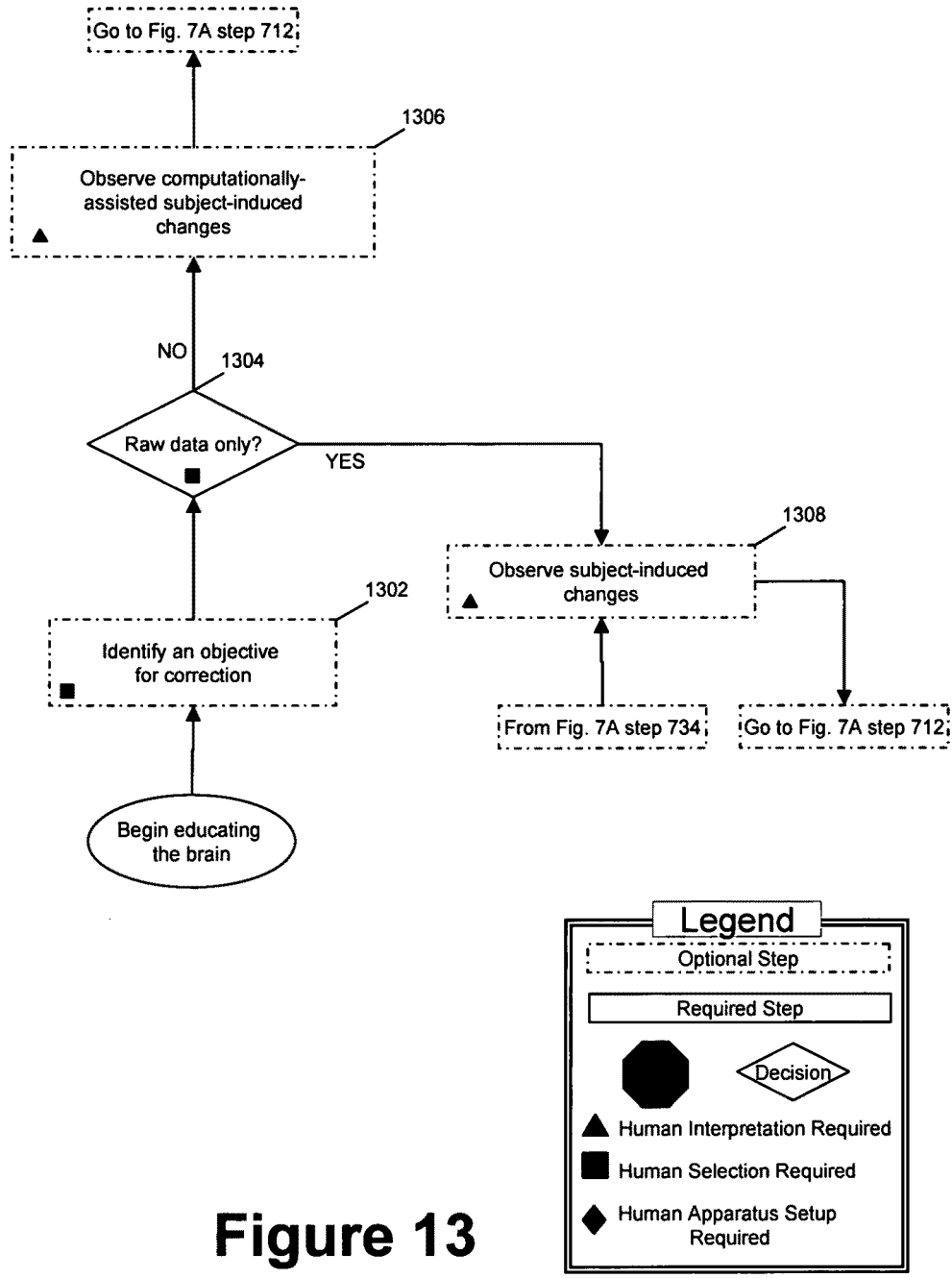
FIG. 13 depicts a flowchart which is an extension of FIG. 7 whereby a human operator has decided to utilize the present invention for the purpose of educating the brain.

Methods of Educating the Brain Utilizing the Present Invention—FIG. 13

FIG. 13 depicts how the present invention can be utilized to educate the subject's own brain such that the condition, disease or performance of the subject's brain would improve. It is possible to use the present invention to educate people to modulate their cortical activity by using the results presented using the final presentation method as a form of biofeedback so as to teach the brain to work more effectively or to reduce the occurrence of an ineffective or abnormal state or process.

Step 1302 is the first step in this application, which is to identify an objective for correction or improvement, i.e. the subject (or the subject with the assistance of a therapist) must opt either to train a desirable electrical activity to occur, or to decide to train an undesirable activity so that it does not occur. For example, if a subject has difficulty concentrating, then the subject may want to improve on the ability to suppress alpha-band electrical activity located in the posterior of the cerebral cortex. A system of rewards and punishments may be used to encourage desirable patterns and discourage unwanted patterns.

The subject then has the choice in decision step 1304, to look at raw data only, or data that has been processed in an assistive manner. Raw data in this case is defined as localized electrical activity that has not had any algorithms such as those mentioned in FIG. 8 performed on the data.

If the subject chooses to observe raw data only, then the subject may choose to interpret it then examine it using the final presentation method, which would involve FIG. 7A step 734, or the subject could remain passive and just examine it without application-specific interpretation by proceeding to FIG. 7A step 712.

If the subject chooses to observe the localized electrical activity that has been computationally assisted via a previously described algorithm, then the algorithm would provide the necessary evidence, especially if there had been a research trial completed on the particular objective for correction or improvement. The subject would then examine the computationally assisted localized electrical activity using the final presentation method, which would involve FIG. 7A step 712.

At this point, the subject would then attempt to enact a mental change to attempt to achieve the objective.

Methods of Entertaining Utilizing the Present Invention—FIG. 14

FIG. 14 depicts how the present invention may be utilized to entertain the subject. Entertaining is defined as the enjoyment or excitement obtained by a subject upon seeing a display of his or her own electrical activity.

Step 1402 is a decision step asking whether the entertainment application involves autonomous algorithms to process the localized electrical activity.

If the application does not involve autonomous processing, then the subject would then watch his or her own localized electrical activity utilizing the final presentation method, in FIG. 7A step 712.

If the application does involve autonomous processing, then the subject would be able to utilize algorithms such as those previously described to recognize patterns automatically which can then in turn be utilized to manipulate a game character or visually entertaining display which ultimately is presented using the final presentation method to display a visual change in the character (FIG. 7A step 712). In this instance the character may be an image of a person or an object. There are a number of options as to which localized signals are harnessed to manipulate the character. The movement of the character on the screen could be linked to electrical activity with is non-volitional, in which case the movement of the figure would be under involuntary control. However, if volitional signals from the motor cortex were localized and captured, then it is possible to have the characters moving according to the volition of the operator.

Figure 15:
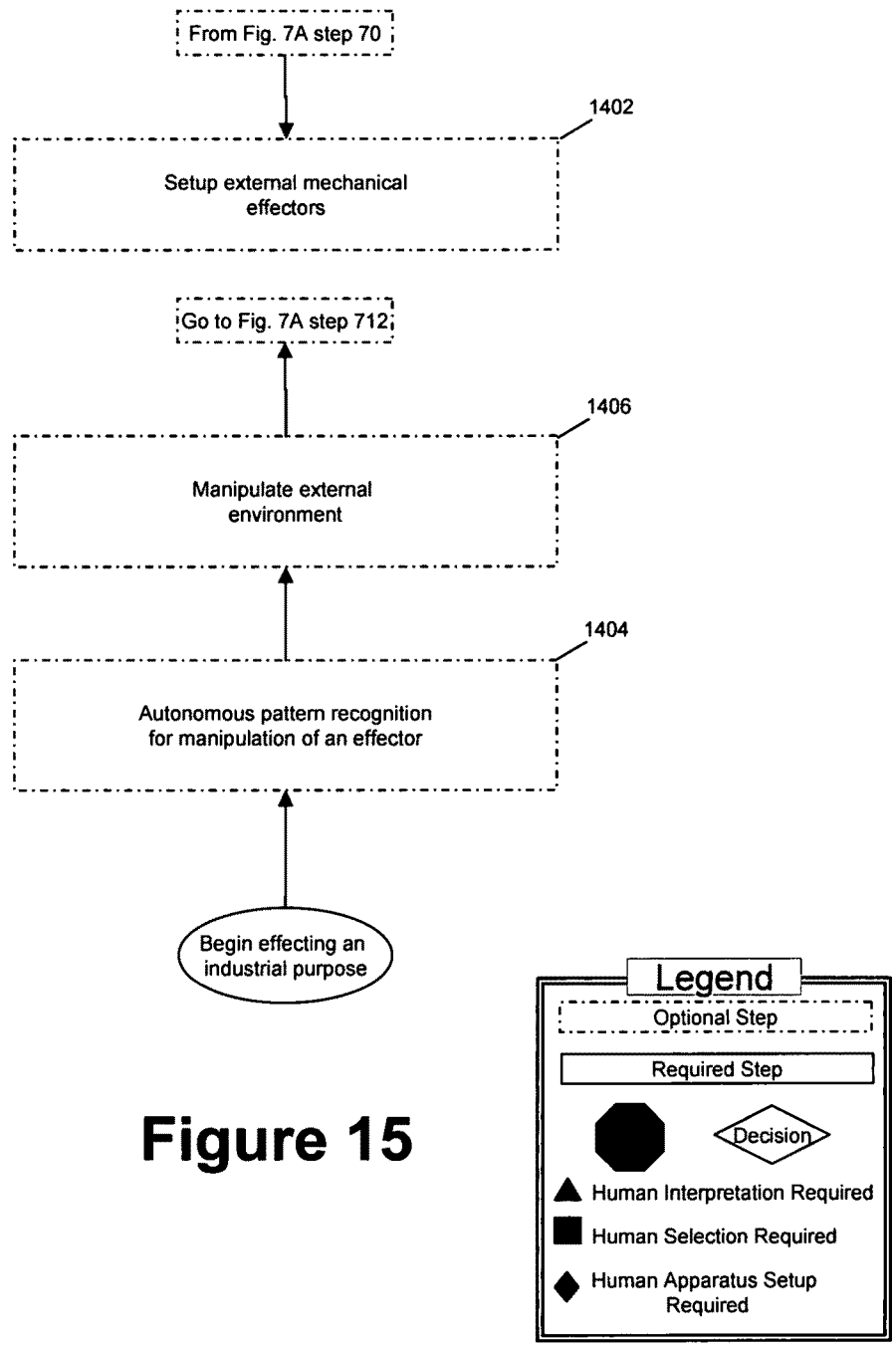
FIG. 15 depicts a flowchart which is an extension of FIG. 7 whereby a human operator has decided to utilize the present invention for the purpose of effecting an industrial purpose.

Methods of Effecting an Industrial Purpose Utilizing the Present Invention—FIG. 15

FIG. 15 depicts how the present invention may be utilized to effect an industrial purpose.

It is possible to isolate localized electrical activity emanating from a subject and then to capture it and activate a change in the environment using an effector. Effectors can be mechanical, as in the case of a robotic arm; physical as when causing changes in temperature: or chemical, whereby a chemical changes are produced.

Step 1402 is when an effector would be setup, leading into FIG. 7A step 70, when other devices are to be setup.

Step 1404 entails the use of algorithms to autonomously recognize certain patterns and capture them so as to activate an external effector to produce a tangible effect on the surrounding environment. Examples include industrial processes to control an external mechanical device, such as an assembly arm, or other industrial robots. The method of pattern recognition may involve one of the previously described algorithms or approaches, specifically from FIG. 8, but it also may require the development of new algorithms to account for the fine control that may be required of certain effectors. In order for the environmental manipulation to be planned and meaningful volitional signals emanating from the frontal lobe of the cerebral cortex, and especially the areas of the brain involved in voluntary motor control will likely need to be isolated, then captured, and finally utilized to activate an effector in step 1406.

In addition, it is possible to add a transmitter, which is in turn connected to a receiver and finally connected to a remote effector in order to produce an industrial change in the environment at a remote location.

Alternative Embodiments of the Present Invention

An alternate embodiment of the invention is directed towards a method of performing near-real time three-dimensional display and analysis with multiple forms of near-real time statistical analysis and quantification using state of the art components including a customized solution space (based on the subject's own cerebral cortex isolated from his or her own MRI or other appropriate brain imaging methodology, using accepted techniques currently in use), an electrode digitizer (a device that accurately measures the electrode positions on the subject's scalp in 3D space), ultrahigh sampling EEG amplifiers/recorders (>20 KHz, so as to sample the cortical activity with great rapidity to allow for generating as many pictures of the cortex as possible per second); the most accurate inverse solution approximations which would allow for the display of voxels with the highest possible spatial resolution despite computational expense; the fastest computers available on the market; and large and/or multiple high resolution screens. This embodiment would be especially useful for imaging changes occurring over extremely short time intervals, and in which multiple forms of analysis are needed to clarify the cortical activity.

In one embodiment of the present invention, data generated using an inverse solution is analyzed by a microcomputer which identifies specific danger signals. This microcomputer is in turn connected to an alarm such as a bell which alerts medical personnel to possible danger to the patient. This embodiment can be without the use of imaging or the display of localized electrical activity. This embodiment represents a portable version of the invention.

An alternate embodiment of the portable invention entails integration with telemedicine methods including transmitters and receivers so that the signals and data are communicated to a second location where clinicians can view and interpret the data for a patient that is remote to them. Ambulatory monitoring of persons that are conscious and can walk may be performed using miniature amplifiers.

Another embodiment of the invention is directed at a method of monitoring electrical activity in sleep and as an aid in the quantification and analysis of sleep stages and as an aid to the diagnosis of sleep disorders. In this embodiment, it is possible to perform near-real time three-dimensional display and analysis of known clinically important waveforms and frequency bands including alpha, beta, delta and theta within sleep activity in separate windows on a screen or screens simultaneously, By combining elements of the present invention with existing techniques involving physiological monitoring devices of parameters that are used in the field of sleep medicine such as oxygenation, or heart rate, it is possible to create an improved form of polysomnography.

The present invention should not be considered limited to the particular examples described above, but rather should be understood to cover aspects of the invention as fairly set out in the attached claims. Various modifications, equivalent processes as well as numerous structures to which the present invention may be applicable will be readily apparent to those of skill in the art to which the present invention is directed upon review of the specifications.

We claim:

1. A method for near-real time three-dimensional localization of electrical activity in the brain comprising:
   applying electrodes to a subject's scalp and associated connectors;
   connecting the electrodes to an amplifier/recorder and connecting the amplifier/recorder to a computer;
   utilizing said amplifier/recorder to receive electrical signals transmitted through said subject's scalp;
   capturing the electrical signals from said amplifier/recorder with said computer continuously as to provide respective time varying electrical signals, wherein capturing the electrical signals comprises sampling sets of digital values from the electrodes at an associated sampling rate corresponding to frames of captured electroencephalographic (EEG) data;
   processing said time varying electrical signals, using said computer, via an inverse solution approximation to provide a series of representations of localized electrical activity originating from said subject's brain on a three-dimensional solution space representing the subject's brain, such that each representation of the series of representations of localized electrical activity comprises a current density vector for each of a plurality of locations within the three-dimensional solution space and being calculated as a product of a corresponding frame of captured EEG data and a transformation matrix; and
   presenting the series of representations of the localized electrical activity to a human operator in near-real time.

2. The method of claim 1 wherein the series of representations of the quantified localized electrical activity are presented via a final presentation method selected from any using a single screen display with one window, using a using a single screen display with multiple windows, using a multiple screen display with single windows, using a multiple screen display with each screen having multiple windows, and using a speaker to generate sound.

3. The method of claim 2 wherein said human operator is aided in drawing conclusions about the subject to perform a wide variety of useful tasks.

4. The method of claim 1 wherein said series of representations of the quantified localized electrical activity is displayed as a stream of images.

5. The method of claim 4 wherein the series of representations of the quantified localized electrical activity is presented as the current density vectors mapped to voxels that have been arranged in the shape of the solution space.

6. The method of claim 5 wherein said voxels are displayed graphically utilizing a tool to manipulate the graphical display and analysis of voxels, said tool comprising one of additive blending, spatial filtering based on a selected region of interest, spatial filtering based on neuroanatomical information, and selective display of cortical shells.

7. The method of claim 5 wherein said stream of images is displayed graphically utilizing a tools to modify graphically displayed results, said tool providing one of display of electrode positions, axis marking, and display of the name, location, and current density of a selected voxel.

8. The method of claim 4 wherein said quantified localized electrical activity is displayed graphically utilizing a tool to analyze and graphically display localized electrical activity, said tool providing one of display of the electrical activity as two-tailed three dimensional current density vector entities, display of the electrical activity as only directional current density information, and limitation of the displayed voxels according to a threshold level of electrical activity.

9. The method of claim 1 wherein said series of representations of the quantified localized electrical activity is displayed as a stream of alphanumeric text.

10. The method of claim 1 wherein said series of representations of the quantified localized electrical activity is simultaneously presented with additional near-real time information selected from any of electroencephalographic signals from said subject, video image signals from said subject, physiological signals from said subject, and audio signals from said subject.

11. The method of claim 1 wherein said quantified localized electrical activity is used for the purpose of aiding in researching localized brain electrical activity and to discover new characteristics of the brain.

12. The method of claim 11 further including:
displaying the series of representations as a series of images;
observing said series of images for gross phenomena; and
developing refined analysis based upon observed gross phenomena.

13. The method of claim 11 wherein said subject is healthy and wherein said subject's quantified localized electrical activity is autonomously contributing in near-real time to generating a normative dataset.

14. The method of claim 11 further wherein said subject is pathological and wherein said subject's quantified localized electrical activity is autonomously contributing in near-real time to generating an abnormal dataset.

15. The method of claim 11 further wherein said subject's quantified localized electrical activity is autonomously compared with a statistical test in near-real time to any one or a combination of the following:
i) an abnormal dataset consisting of one or more subjects,
ii) an normal dataset consisting of one or more subjects,
iii) said subject's own normal dataset,
iv) said subject's own abnormal dataset.

16. The method of claim 11 wherein said subject's quantified localized electrical activity is autonomously contributing in near-real time to generating a correlative dataset.

17. The method of claim 1 further including recording the results of said processing of time varying electrical signals on a recording medium.

18. The method of claim 17 further including playback of said recording.

19. The method of claim 1, further comprising providing a stimulus to the subject, the stimulus comprising one of an auditory stimulus, a visual stimulus, a tactile stimulus, a psychological stimulus, an olfactory stimulus, a chemical stimulus, a painful stimulus, an electromagnetic stimulus, and a thermal stimulus.

20. The method of claim 1, wherein presenting the series of representations of the localized electrical activity to a human operator in near-real time comprises activating an external effector arranged so as to have a tangible effect on an object in the surrounding environment in response the series of representations of localized electrical activity as to provide a brain computer interface.

21. A method for researching to establish a set of at least one parameter indicative of mental, psychological and physical brain processes, states, conditions, disorders, treatment targets, normal and abnormal brain activity, brain responses to stimuli, deterioration or improvement in a condition, or truthfulness and lies, comprising the steps of:
A) applying electrodes to a subject's scalp;
B) capturing electrical signals from the electrodes, wherein capturing the electrical signals comprises sampling a set of digital values from the electrodes at an associated sampling rate and filtering the set of digital values to provide frames of captured electroencephalographic (EEG) data at the associated sampling rate;
C) processing the captured electrical signals by an inverse solution approximation to produce a dataset of current density vectors with each value corresponding to electrical activity at a specific three dimensional location in the subject's brain, each dataset of current density vectors being calculated as a product of a corresponding frame of captured EEG data and a transformation matrix;
D) analyzing the dataset to provide said set of parameters; and
E) displaying a human-comprehensible representation of the set of parameters in near-real time.

22. The method of claim 21, wherein analyzing the dataset comprises applying a filtering operation to the dataset of current density-vectors, such that the human-comprehensible representation of the current density vectors represents less than all of the dataset.

23. A non-transitory computer readable medium storing machine executable instructions, the machine executable instructions being executable by a processor to perform a method to establish a set of at least one parameter indicative of mental, psychological and physical brain processes, states, conditions, disorders, treatment targets, normal and abnormal brain activity, brain responses to stimuli, deterioration or improvement in a condition, or truthfulness and lies, comprising the steps of:
processing captured electrical signals, captured at an associated sampling rate, by an inverse solution approximation to produce a dataset of current density vectors with each value corresponding to electrical activity at a specific three dimensional location in the subject's brain, such that a given dataset of current density vectors is calculated as a product of a corresponding frame of captured EEG data and a transformation matrix;

analyzing the dataset to provide said set of parameters and;

displaying a human-comprehensible representation of the set of parameters in near-real time.

24. A system for near-real time three-dimensional localization of electrical activity in the brain comprising:

electrodes configured for application to a subject's scalp;

an amplifier/recorder operatively connected to the electrodes;

a computer, including at least a processor and a non-transitory computer readable medium, operatively connected to the amplifier/recorder and configured to receive electrical signals transmitted through said subject's scalp, capture the electrical signals from said amplifier/recorder continuously as to provide respective time varying electrical signals, wherein capturing the electrical signals comprises sampling sets of digital values from the electrodes at an associated sampling rate corresponding to frames of captured electroencephalographic (EEG) data, and process said time varying electrical signals via an inverse solution approximation to provide a series of representations of localized electrical activity originating from said subject's brain on a three-dimensional solution space representing the subject's brain, such that each representation of the series of representations of localized electrical activity comprises a current density vector for each of a plurality of locations within the three-dimensional solution space and being calculated as a product of a corresponding frame of captured EEG data and a transformation matrix; and an output device, operatively connected to the computer, to present the series of representations of the localized electrical activity to a human operator in near-real time.

* * * * *